(12) United States Patent
Carew et al.

(10) Patent No.: US 9,926,326 B2
(45) Date of Patent: Mar. 27, 2018

(54) SUBSTITUTED THIOXANTHENONE AUTOPHAGY INHIBITORS

(71) Applicant: THE CLEVELAND CLINIC FOUNDATION, Cleveland, OH (US)

(72) Inventors: Jennifer Carew, Cleveland, OH (US); James G. Phillips, Cleveland, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 15/324,969

(22) PCT Filed: Jul. 14, 2015

(86) PCT No.: PCT/US2015/040370
§ 371 (c)(1),
(2) Date: Jan. 9, 2017

(87) PCT Pub. No.: WO2016/011022
PCT Pub. Date: Jan. 21, 2016

(65) Prior Publication Data
US 2017/0210746 A1 Jul. 27, 2017

Related U.S. Application Data

(60) Provisional application No. 62/024,098, filed on Jul. 14, 2014.

(51) Int. Cl.

| | |
|---|---|
| C07D 487/04 | (2006.01) |
| C07D 409/12 | (2006.01) |
| A61K 31/4709 | (2006.01) |
| C07D 335/16 | (2006.01) |
| A61K 31/382 | (2006.01) |
| A61K 31/519 | (2006.01) |
| A61K 45/06 | (2006.01) |

(52) U.S. Cl.
CPC .......... *C07D 487/04* (2013.01); *A61K 31/382* (2013.01); *A61K 31/4709* (2013.01); *A61K 31/519* (2013.01); *A61K 45/06* (2013.01); *C07D 335/16* (2013.01); *C07D 409/12* (2013.01)

(58) Field of Classification Search
CPC .................................................... C07D 487/04
USPC ........................................................ 549/23
See application file for complete search history.

(56) References Cited

U.S. PATENT DOCUMENTS

| | | |
|---|---|---|
| 8,524,762 B2 | 9/2013 | Nawrocki et al. |
| 2011/0275696 A1 | 11/2011 | Nawrocki et al. |
| 2014/0050696 A1 | 2/2014 | Amaravadi et al. |

OTHER PUBLICATIONS

Sharghi et al., J. of the Iranian Chem. Soc. (2008), vol. (suppl.), S33-S39.*
Amaravadi RK, Winkler JD. Lys05: A new lysosomal autophagy inhibitor. Autophagy. 2012;8(9):1383-1384. doi:10.4161/auto.20958.
Barnard RA, Wittenburg LA, Amaravadi RK, Gustafson DL, Thorburn A, Thamm DH. Phase I clinical trial and pharmacodynamic evaluation of combination hydroxychloroquine and doxorubicin treatment in pet dogs treated for spontaneously occurring lymphoma. Autophagy. 2014;10(8):1415-1425. doi:10.4161/auto.29165.
Beaujouin M, Baghdiguian S, Glondu-Lassis M, Berchem G, Liaudet-Coopman E. Overexpression of both catalytically active and -inactive cathepsin D by cancer cells enhances apoptosis-dependent chemo-sensitivity. Oncogene. 2006;25(13):1967-1973. doi:10.1038/sj.onc.1209221.
Bjorkoy G, Lamark T, Brech A, et al. p62/SQSTM1 forms protein aggregates degraded by autophagy and has a protective effect on huntingtin-induced cell death. The Journal of Cell Biology. 2005;171(4):603-614. doi:10.1083/jcb.200507002.
Carew JS, Medina EC, Esquivel II JA, et al. Autophagy inhibition enhances vorinostat-induced apoptosis via ubiquitinated protein accumulation. Journal of Cellular and Molecular Medicine. 2010;14(10):2448-2459. doi:10.1111/j.1582-4934.2009.00832.x.
Carew JS, Nawrocki ST, Kahue CN, et al. Targeting autophagy augments the anticancer activity of the histone deacetylase inhibitor SAHA to overcome Bcr-Abl-mediated drug resistance. Blood. 2007;110(1):313-322. doi:10.1182/blood-2006-10-050260.
Carew JS, Nawrocki ST, Reddy VK, et al. The Novel Polyamine Analog CGC-11093 Enhances the Anti-Myeloma Activity of Bortezomib. Cancer research. 2008;68(12):4783-4790. doi:10.1158/0008-5472.CAN-07-6483.
Carew, Jennifer S., et al. "Lucanthone is a novel inhibitor of autophagy that induces cathepsin D-mediated apoptosis." Journal of Biological Chemistry 286.8 (2011): 6602-6613.
Carew, Jennifer S., Kevin R. Kelly, and Steffan T. Nawrocki. "Autophagy as a target for cancer therapy: new developments." Cancer management and research 4 (2012): 357.
Carew, Jennifer S., Steffan T. Nawrocki, and John L. Cleveland. "Modulating autophagy for therapeutic benefit." Autophagy 3.5 (2007): 464-467.

(Continued)

*Primary Examiner* — Taofiq A Solola
(74) *Attorney, Agent, or Firm* — Tarolli, Sundheim, Covell & Tummino LLP

(57) ABSTRACT

Autophagy inhibitors useful for the treatment of cancer and other diseases are described. The autophagy inhibitors are a compound of formula: I wherein $R^1$ is a group selected from lower alkyl, lower alkyl amide, lower alkyl ester, lower alkyl ketone, and lower alkyl ether; $R^2$ and $R^3$ are H or a group selected from cycloalkyl, lower alkyl, lower alkyl amide, lower alkyl ester, lower alkyl ketone, and lower alkyl ether; $R^4$ is a heteroaryl group; and L is a —$(CH_2)_n$—X—$(CH_2)_n$— group, wherein n is 1, 2, 3, or 4, X is absent, O, S, or N—$R^5$, wherein $R^5$ is H or a lower alkyl group, or a pharmaceutically acceptable salt thereof.

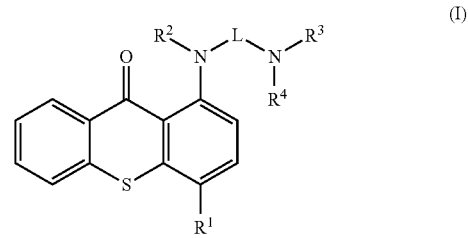

17 Claims, 9 Drawing Sheets

(56) References Cited

OTHER PUBLICATIONS

Del Rowe, John D., et al. "Accelerated regression of brain metastases in patients receiving whole brain radiation and the topoisomerase II inhibitor, lucanthone." International Journal of Radiation Oncology* Biology* Physics 43.1 (1999): 89-93.
Guo JY, Chen H-Y, Mathew R, et al. Activated Ras requires autophagy to maintain oxidative metabolism and tumorigenesis. Genes & Development. 2011;25(5):460-470. doi:10.1101/gad.2016311.
Mahalingam, Devalingam, et al. "Combined autophagy and HDAC inhibition: a phase I safety, tolerability, pharmacokinetic, and pharmacodynamic analysis of hydroxychloroquine in combination with the HDAC inhibitor vorinostat in patients with advanced solid tumors." Autophagy 10.8 (2014): 1403-1414.
McAfee Q, Zhang Z, Samanta A, et al. Autophagy inhibitor Lys05 has single-agent antitumor activity and reproduces the phenotype of a genetic autophagy deficiency. Proceedings of the National Academy of Sciences of the United States of America. 2012;109(21):8253-8258. doi:10.1073/pnas.1118193109.
Rangwala R, Chang YC, Hu J, et al. Combined MTOR and autophagy inhibition: Phase I trial of hydroxychloroquine and temsirolimus in patients with advanced solid tumors and melanoma. Autophagy. 2014;10(8):1391-1402. doi:10.4161/auto.29119.
Rangwala R, Leone R, Chang YC, et al. Phase I trial of hydroxychloroquine with dose-intense temozolomide in patients with advanced solid tumors and melanoma. Autophagy. 2014;10(8):1369-1379. doi:10.4161/auto.29118.
Rosenfeld MR, Ye X, Supko JG, et al. A phase I/II trial of hydroxychloroquine in conjunction with radiation therapy and concurrent and adjuvant temozolomide in patients with newly diagnosed glioblastoma multiforme. Autophagy. 2014;10(8):1359-1368. doi:10.4161/auto.28984.
Sharghi, H., and A. Salimi Beni. "Synthesis and Nucleophilic Substitution Reaction of 1-Halo-9H-thioxanthen-9-one." Journal of the Iranian Chemical Society 1.5 (2008): S33-S39.
Vogl DT, Stadtmauer EA, Tan K-S, et al. Combined autophagy and proteasome inhibition: A phase 1 trial of hydroxychloroquine and bortezomib in patients with relapsed/refractory myeloma. Autophagy. 2014;10(8):1380-1390. doi:10.4161/auto.29264.
International Search report and Written Opinion for corresponding PCT/US2015/040370, dated Oct. 16, 2015, pp. 1-7.
Sehgal, A. R., et al. "You eat what you are: autophagy inhibition as a therapeutic strategy in leukemia." Leukemia 29.3 (2015): 517.
Fuchs Y, Steller H. Programmed Cell Death in Animal Development and Disease. Cell. 2011;147(4):742-758. doi:10.1016/j.cell.2011.10.033.
Thapalia BA, Zhou Z, Lin X. Autophagy, a process within reperfusion injury: an update. International Journal of Clinical and Experimental Pathology. 2014;7(12):8322-8341.
Codogno, Patrice, and Alfred J. Meijer. "Autophagy: a potential link between obesity and insulin resistance." Cell metabolism 11.6 (2010): 449-451.
Rubinsztein, David C., Guillermo Mariño, and Guido Kroemer. "Autophagy and aging." Cell 146.5 (2011): 682-695.
Virgin, Herbert W, and Beth Levine. "Autophagy Genes in Immunity." Nature immunology 10.5 (2009): 461-470. PMC. Web. Oct. 30, 2017.
Carew, Jennifer S, Kevin R Kelly, and Steffan T Nawrocki. "Autophagy as a Target for Cancer Therapy: New Developments." Cancer Management and Research 4 (2012): 357-365. PMC. Web. Oct. 30, 2017.
Haendeler, Judith, et al. "Cathepsin D and H2O2 Stimulate Degradation of Thioredoxin-1 Implication for Endothelial Cell Apoptosis." Journal of Biological Chemistry 280.52 (2005): 42945-42951.
Liaudet-Coopman, Emmanuelle, et al. "Cathepsin D: newly discovered functions of a long-standing aspartic protease in cancer and apoptosis." Cancer letters 237.2 (2006): 167-179.
Hidvegi, et al. An Autophagy-Enhancing Drug Promotes Degradation of Mutant α1-Antitrypsin Z and Reduces Hepatic Fibrosis, Science Jul. 9, 2010: 229-232.
Pareek, Anil, et al. "Efficacy and safety of hydroxychloroquine in the treatment of type 2 diabetes mellitus: a double blind, randomized comparison with pioglitazone." Current medical research and opinion 30.7 (2014): 1257-1266.

* cited by examiner

SUBSTITUTED THIOXANTHENONE AUTOPHAGY INHIBITORS

CROSS-REFERENCE TO RELATED APPLICATIONS

This application claims priority from U.S. Provisional Application Ser. No. 62/024,098, filed Jul. 14, 2014, the entire contents of which is incorporated herein by reference.

BACKGROUND

Autophagy is an evolutionarily conserved mechanism of lysosomal proteolysis that is characterized by the formation of double-membraned vesicles (autophagosomes) that envelop bulk cellular material and/or organelles. Autophagosomes subsequently fuse with lysosomes and the degradation of their cargo is mediated by lysosomal proteases. Autophagy is used for the turnover of organelles and proteins with long half-lives and also functions to generate alternative sources of metabolic fuel via nutrient recycling under stress conditions. Within the context of cancer, preclinical studies conducted with an Akt-driven tumor model established that autophagy is preferentially activated in malignant cells during the early stages of tumorigenesis. Although multiple subsequent studies have confirmed that autophagy functions as mechanism of tumor suppression via the elimination of defective pre-malignant cells, overwhelming evidence supports a major role for autophagic degradation in the maintenance of bioenergetic homeostasis under stress conditions including hypoxia and nutrient deprivation. Additionally, autophagy has emerged as an important mechanism of resistance to radiation, classical chemotherapy, and targeted anticancer agents due to its ability to augment the survival capacity of malignant cells. Many recent studies have shown that pharmacological or genetic inhibition of autophagy significantly enhances the efficacy of therapeutic agents. Carew et al., Cancer Manag Res.: 4:357-365 (2012). These collective findings demonstrate that inhibition of autophagy is a promising strategy with broad potential applications.

Chloroquine (CQ) and hydroxychloroquine (HCQ) have been used for decades to treat malaria, rheumatoid arthritis, and lupus and represent two of a very small group of FDA-approved drugs that disrupt lysosomal function and consequently inhibit autophagy. Currently, CQ and HCQ are the best studied FDA-approved drugs that are known to inhibit autophagy. More than 30 phase I and II clinical trials utilizing CQ or HCQ in combination with anticancer agents have been initiated during the last 6 years. However; the clinical applications of CQ/HCQ with respect to autophagy inhibition may ultimately be limited due to their known ability to induce ocular toxicity and the possibility that they may not completely disrupt autophagy at doses that are safe and well tolerated. New autophagy inhibitors are desperately needed. LUC (Miracil D) is a thioxanthone drug that crosses the blood-brain barrier and has been extensively used as an anti-schistome agent. Del Rowe et al., Int J Radiat Oncol Biol Phys.: 43(1): 89-93 (1999). The drug also blocks topoisomerase II activity and has been reported to inhibit AP endonuclease (APE1), an important enzyme in DNA base excision repair. Based on these properties, LUC is currently being investigated as a sensitizer to chemotherapy and radiation. The inventors recently discovered a novel mechanism of action for lucanthone that is characterized by the disruption of lysosomal function, inhibition of autophagy, and induction of apoptosis (U.S. Pat. No. 8,524,762). Similar to CQ, these effects enable LUC to potentiate the efficacy of other standard of care agents. LUC-induced apoptosis occurred through a p53-independent mechanism and notably, LUC displayed more potent anticancer activity (approximately 10× greater) compared to CQ. Carew et al., J Biol Chem.; 286(8): 6602-6613 (2011). Despite these reported properties, to date, no comprehensive structure-activity relationship (SAR) studies have been performed to optimize and illuminate the autophagic inhibition triggered by LUC or CQ/HCQ.

SUMMARY OF THE INVENTION

Autophagy contributes to malignant transformation, disease progression, and drug resistance within the context of malignancy and is also a critical factor in the pathogenesis of many other non-malignant disorders. Its inhibition is therefore an appealing therapeutic strategy that may have broad clinical applications. However, the limited availability of clinical agents that disrupt autophagy has precluded rigorous evaluation of this new approach. The inventors have developed novel autophagy inhibitors based on the lucanthone (LUC) and hydroxychloroquine (HCQ) scaffolds and hypothesize that these new agents will have utility for the treatment of a broad range of malignancies and other disease where aberrant lysosomal function contributes to pathogenesis or drug resistance.

Figure 4:
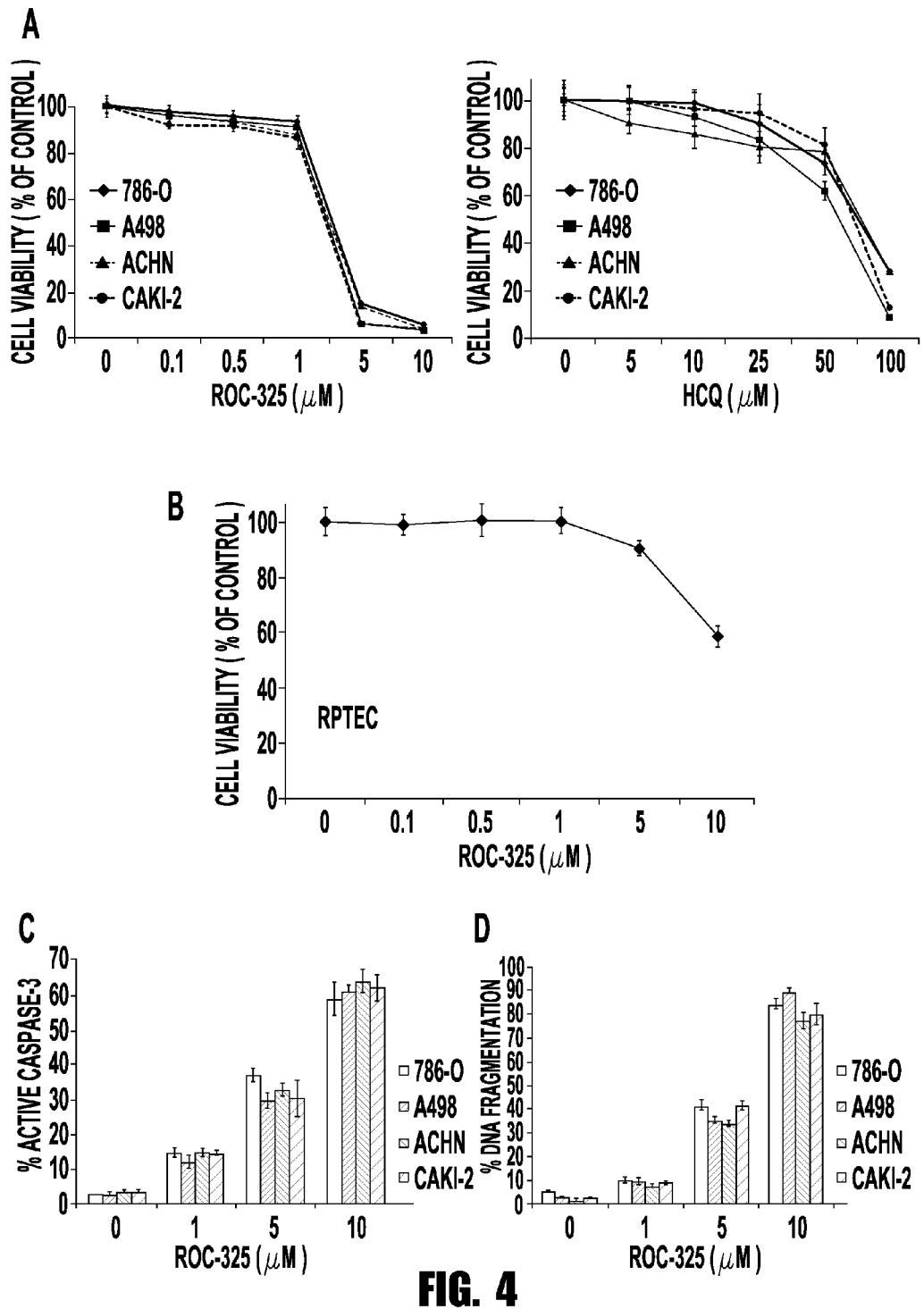

FIG. 4 (A-D) provides graphs showing ROC-325 induces apoptosis and is significantly more effective at reducing the viability of RCC cells than HCQ; A) ROC-325 and HCQ decrease RCC cell line viability. RCC cell lines were treated with varying concentrations of ROC-325 or HCQ for 72 h. Cell viability was measured using the MTT assay. Mean±SD, n=3; B) Normal RPTEC cells are less sensitive to ROC-325. RPTEC cells were treated with the indicated concentrations of ROC-325 and cell viability was determined by MTT assay. Mean±SD, n=3; (C) ROC-325 stimulates caspase-3 activation. RCC cell lines were treated with the indicated concentrations of ROC-325 for 48 h. Active caspase-3 was measured using a FITC-labeled active caspase-3 antibody followed by flow cytometric analysis. Mean±SD, n=3; D) ROC-325 induces DNA fragmentation. RCC cells were treated with varying concentrations of ROC-325 for 48 h. DNA fragmentation was measured by PI-FACS analysis. Mean±SD, n=3.

Figure 5:
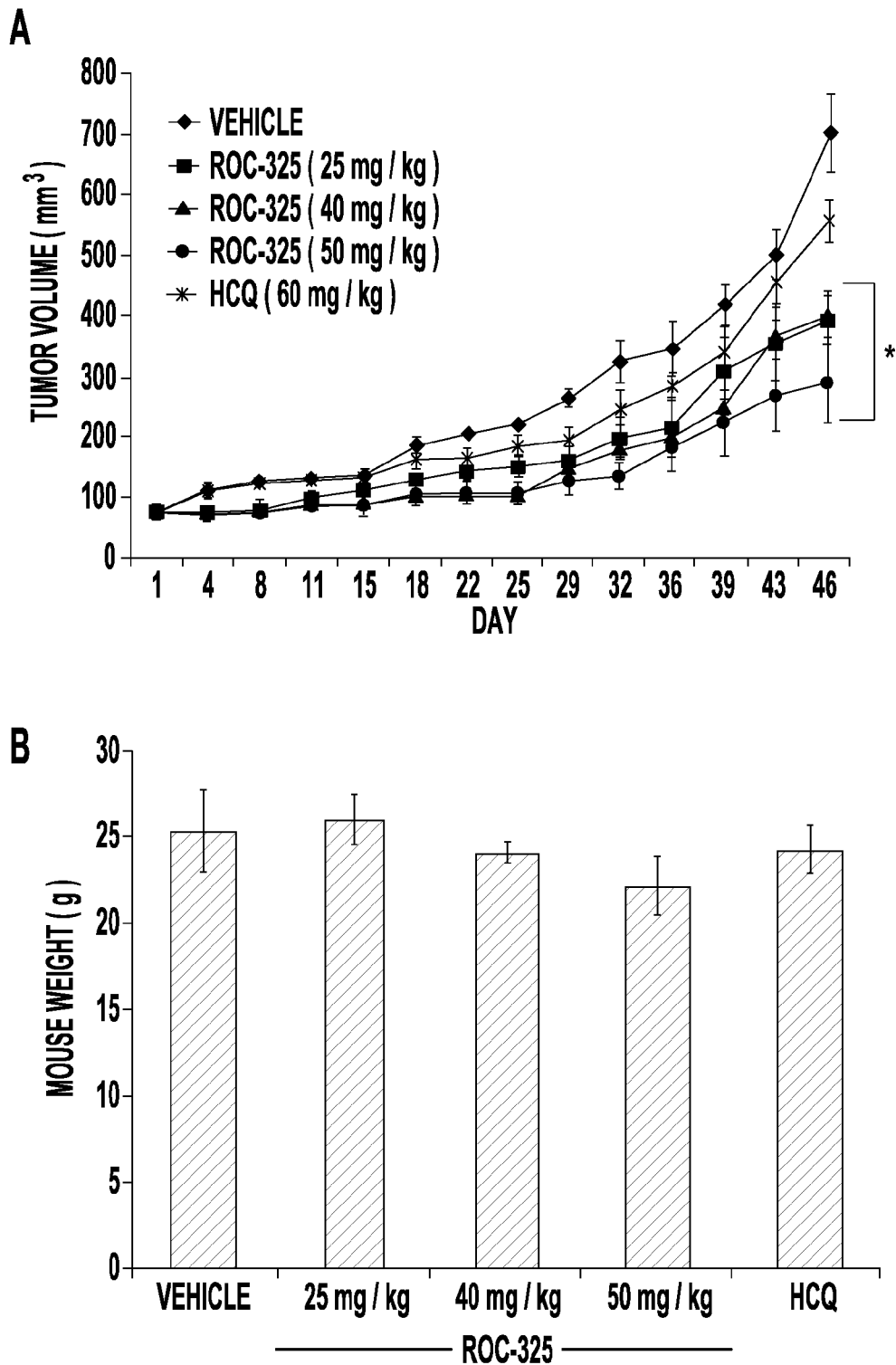

FIG. 5 (A. B) provides graphs showing ROC-325 reduces tumor burden in RCC xenografts. A) 786-O cells were injected into the flanks of nude mice. Mice were pair-matched and randomized into groups when mean tumor burden reached approximately 100 mm³. Mice were treated with 25, 40, or 50 mg/kg ROC-325 PO and 60 mg/kg HCQ IP QD×5 throughout the course of the study. Tumor volumes were measured twice weekly. Mean±SEM, n=5. *Indicates a significant difference compared Vehicle. P<0.05; B) ROC-325 is well tolerated in mice. Body weight was determined at the end of the study (Day 46) to quantify drug-induced weight loss. Mean±SD, n=5.

Figure 6:
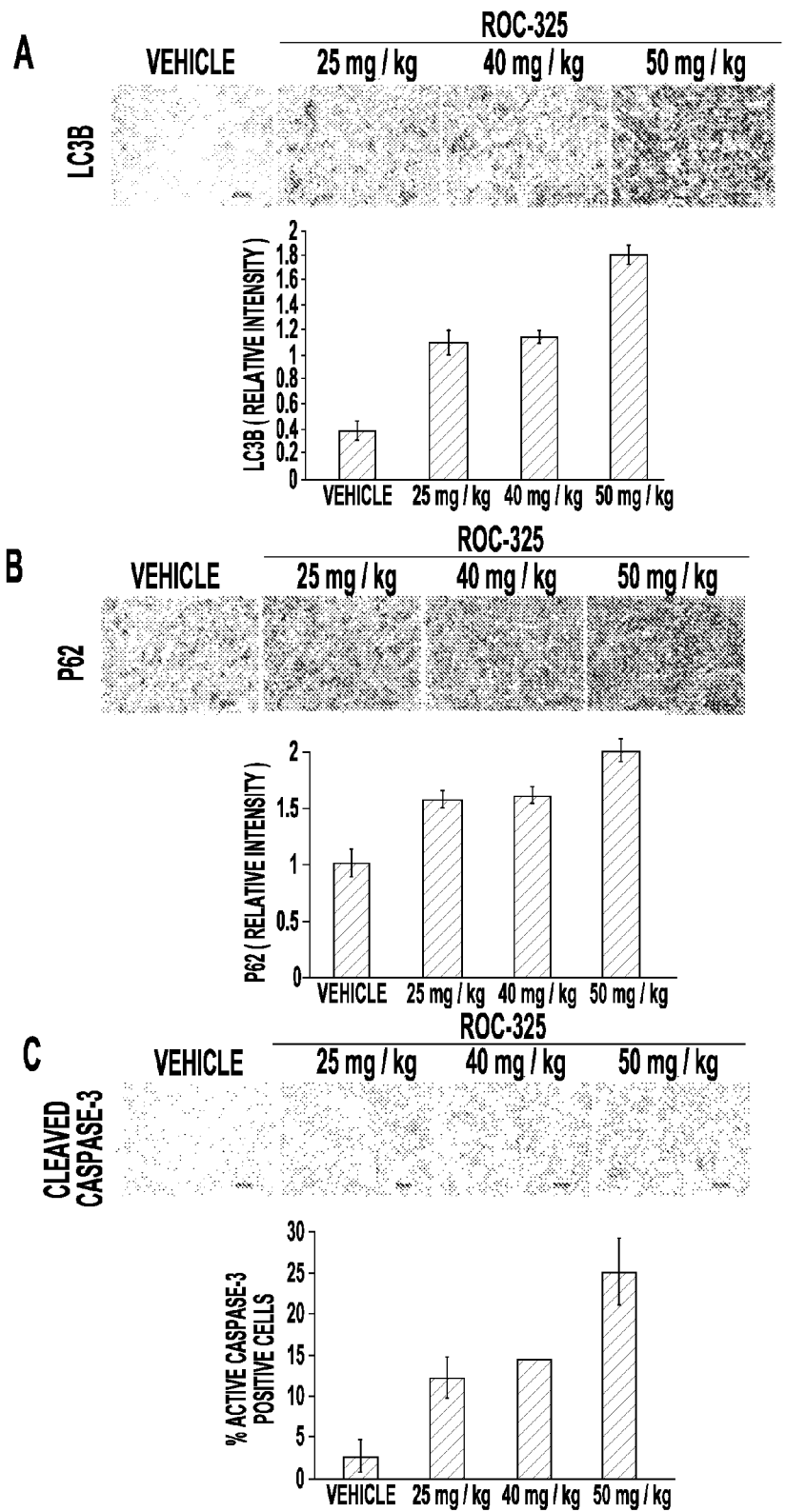

FIG. 6 (A-C) provides graphs and images showing ROC-325 significantly increases LC3B and p62 expression and induces apoptosis in RCC xenografts. A) LC3B immunohistochemistry. Tumors were stained with an anti-LC3B antibody and the relative intensity of expression was quantified by densitometry. Mean±SD, n=5; B) p62 immunohistochemistry. Tumors were stained with an anti-p62 antibody and the relative intensity of expression was quantified by densitometry. Mean±SD, n=5; C) Apoptosis was determined by active caspase-3 immunohistochemistry. Tumors were stained with an antibody to cleaved caspase-3. The percentage of positive stained cells was determined manually under 20× magnification. Mean±SD, n=5.

Figure 7:
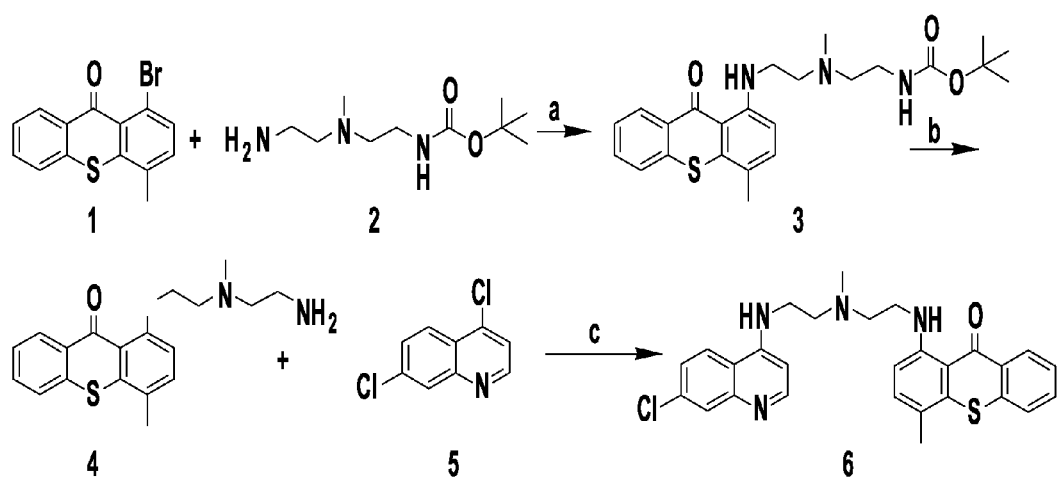

FIG. 7 provides a scheme showing the steps involving conditions (a-c) in the synthesis of ROC-325: a) K₃PO₄, BINAP, Pd(OAc)₂, dioxane, 85° C.; b) 4N HCl in dioxane; c) K₃PO₄, BINAP, Pd(OAc)₂, dioxane, 85° C.; Methanol, 4N HCl in dioxane.

Figure 8:
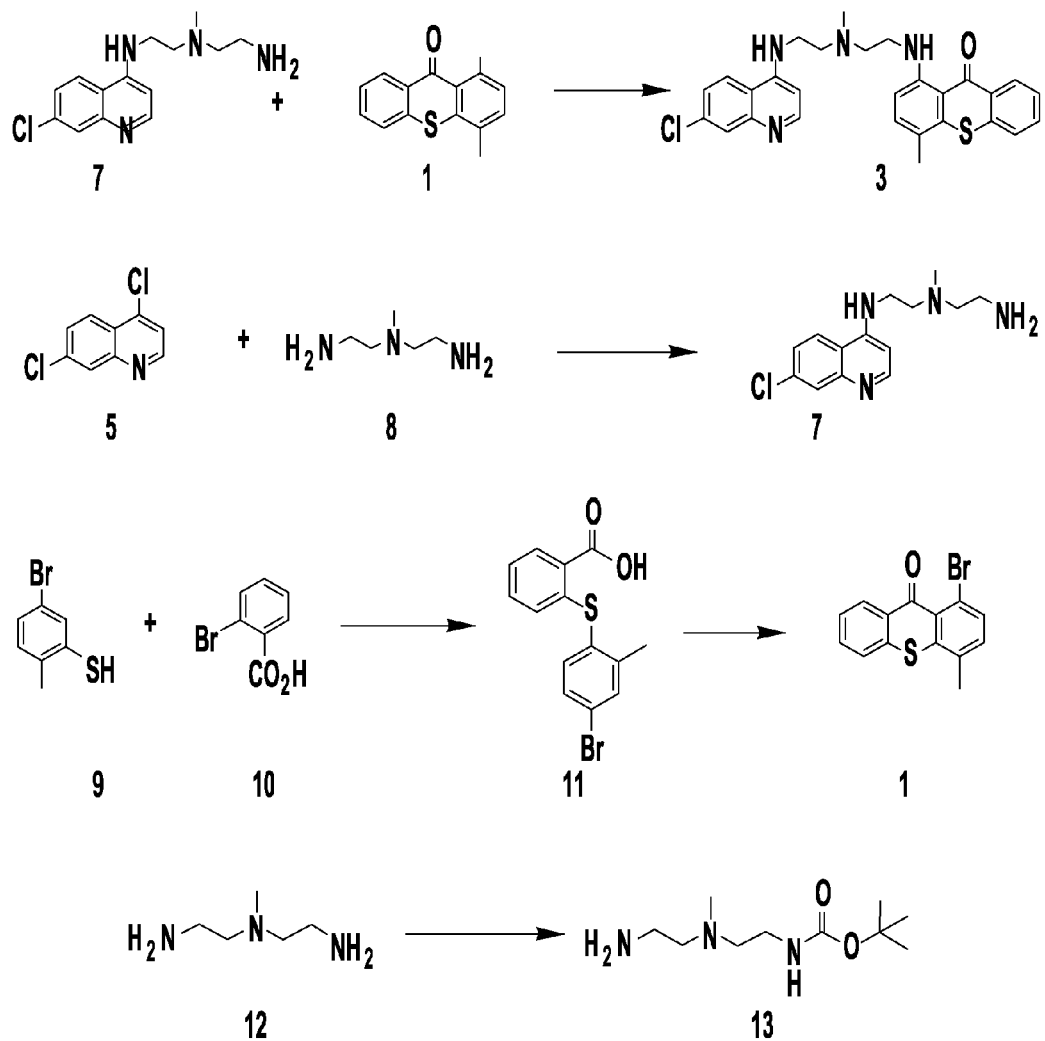

FIG. 8 provides a scheme showing the steps involved in an alternate synthesis of ROC-325.

Figure 9:
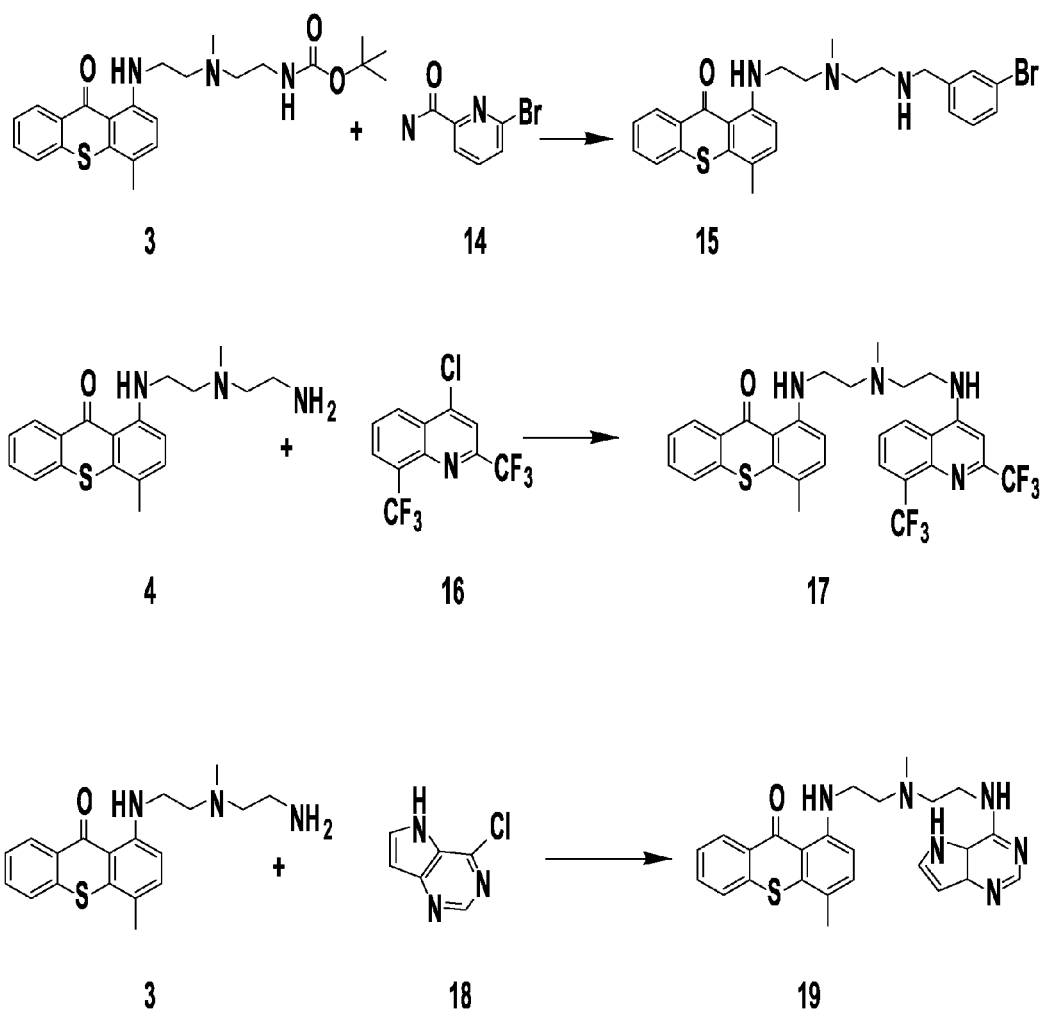

FIG. 9 provides a scheme showing the steps involved in the synthesis of additional thioxanthenone autophagy inhibitors.

DETAILED DESCRIPTION OF THE INVENTION

The present invention provides autophagy inhibitors according to formula I

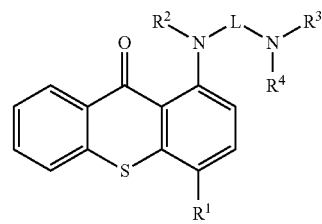

wherein $R^1$ is a group selected from lower alkyl, lower alkyl amide, lower alkyl ester, lower alkyl ketone, and lower alkyl ether: $R^2$ and $R^3$; are H or a group selected from cycloalkyl, lower alkyl, lower alkyl amide, lower alkyl ester, lower alkyl ketone, and lower alkyl ether; $R^4$ is a heteroaryl group; and L is a —$(CH_2)_n$—X—$(CH_2)_n$— group, wherein n is 1, 2, 3, or 4, X is absent, O, S, or N—$R^5$, wherein $R^5$ is H or a lower alkyl group, or a pharmaceutically acceptable salt thereof. The autophagy inhibitors can be used to treat a subject having a disease or condition that responds favorably to autophagy inhibition, such as cancer.

Definitions

The terminology as set forth herein is for description of the embodiments only and should not be construed as limiting of the invention as a whole. Unless otherwise specified, "a," "an," "the," and "at least one" are used interchangeably. Furthermore, as used in the description of the invention and the appended claims, the singular forms "a", "an", and "the" are inclusive of their plural forms, unless contraindicated by the context surrounding such.

The term "compound" is used herein to describe any specific compound or bioactive agent disclosed herein, including any and all stereoisomers (including diastereomers), individual optical isomers (enantiomers) or racemic mixtures, pharmaceutically acceptable salts and prodrug forms. The term compound herein refers to stable compounds. Within its use in context, the term compound may refer to a single compound or a mixture of compounds as otherwise described herein. It is understood that the choice of substituents or bonds within a Markush or other group of substituents or bonds is provided to form a stable compound from those choices within that Markush or other group.

As used herein, the term "organic group" is used for the purpose of this invention to mean a hydrocarbon group that is classified as an aliphatic group, cyclic group, or combination of aliphatic and cyclic groups (e.g., alkaryl and aralkyl groups). In the context of the present invention, suitable organic groups for autophagy inhibitors are those that do not interfere with the compounds anticancer activity. In the context of the present invention, the term "aliphatic group" means a saturated or unsaturated linear or branched hydrocarbon group. This term is used to encompass alkyl, alkenyl, and alkynyl groups, for example.

As used herein, the terms "alkyl", "alkenyl", and the prefix "alk-" are inclusive of straight chain groups and branched chain groups and cyclic groups, e.g., cycloalkyl and cycloalkenyl. Unless otherwise specified, these groups contain from 1 to 20 carbon atoms, with alkenyl groups containing from 2 to 20 carbon atoms. In some embodiments, these groups have a total of at most 10 carbon atoms, at most 8 carbon atoms, at most 6 carbon atoms, or at most 4 carbon atoms. Lower alkyl groups are those including at most 6 carbon atoms. Examples of alkyl groups include haloalkyl groups and hydroxyalkyl groups.

Unless otherwise specified. "alkylene" and "alkenylene" are the divalent forms of the "alkyl" and "alkenyl" groups defined above. The terms. "alkylenyl" and "alkenylenyl" are used when "alkylene" and "alkenylene", respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-". Examples of suitable haloalkyl groups are chloromethyl, trifluoromethyl, and the like. A halo moiety can be chlorine, bromine, fluorine, or iodine.

The terms alkyl amide, alkyl ester, alkyl ketone, and alkyl ether refer to alkyl groups that include one or more oxygen molecules within the alkyl chain. Alkyl amides are represented by the formula R—C(O)—NH—R', Alkyl esters are represented by the formula R—C(O)—O—R', alkyl ketones are represented by the formula R—C(O)—R', and alkyl ethers are represented by the formula R—O—R'. In a lower alkyl amide, ester, ketone, or ether, the entire group, including R and R', will have from 2 to 6 carbon atoms.

Cycloalkyl groups are cyclic alkyl groups containing 3, 4, 5, 6, 7 or 8 ring carbon atoms like cyclopropyl, cyclobutyl, cyclopentyl, cyclohexyl or cyclooctyl, which can also be substituted and/or contain 1 or 2 double bounds (unsaturated cycloalkyl groups) like, for example, cyclopentenyl or cyclohexenyl can be bonded via any carbon atom.

A heterocyclyl group means a mono- or bicyclic ring system in which one or more carbon atoms can be replaced by one or more heteroatoms such as, for example, 1, 2 or 3 nitrogen atoms, 1 or 2 oxygen atoms, 1 or 2 sulfur atoms or combinations of different hetero atoms. The heterocyclyl residues can be bound at any positions, for example on the 1-position, 2-position, 3-position, 4-position, 5-position, 6-position, 7-position or 8-position.

The term "aryl" as used herein includes carbocyclic aromatic rings or ring systems. Examples of aryl groups include phenyl, naphthyl, biphenyl, anthracenyl, phenanthracenyl, fluorenyl and indenyl. Aryl groups may be substituted or unsubstituted.

Unless otherwise indicated, the term "heteroatom" refers to the atoms O, S, or N.

The term "heteroaryl" includes aromatic rings or ring systems that contain at least one ring heteroatom (e.g., O, S, N). In some embodiments, the term "heteroaryl" includes a ring or ring system that contains 2 to 12 carbon atoms, 1 to 3 rings, 1 to 4 heteroatoms, and O, S, and/or N as the heteroatoms. Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, henzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, tetrazinyl, oxadiazolyl, thiadiazolyl, anthracenyl, thioxantheninyl, pyrrolopyrimidiyl and so on.

When a group is present more than once in any formula or scheme described herein, each group (or substituent) is independently selected, whether explicitly stated or not. For example, for the formula —C(O)—NR$_2$ each R group is independently selected.

As a means of simplifying the discussion and the recitation of certain terminology used throughout this application, the terms "group" and "moiety" are used to differentiate between chemical species that allow for substitution or that may be substituted and those that do not so allow for substitution or may not be so substituted. Thus, when the term "group" is used to describe a chemical substituent, the described chemical material includes the unsubstituted group and that group with nonperoxidic O, N, S, Si, or F atoms, for example, in the chain as well as carbonyl groups or other conventional substituents. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, tert-butyl, and the like.

The term "autophagy" is used to describe a catabolic process in cells which involves the degradation of a cell's own components through lysosomes.

"Treat", "treating", and "treatment", etc., as used herein, refer to any action providing a benefit to a patient at risk for or afflicted with a disease, including improvement in the condition through lessening or suppression of at least one symptom, delay in progression of the disease, delay in the onset of the disease, etc. Treatment also includes partial or total inhibition of autophagy in a subject having a disease or condition that responds favorably to autophagy.

As used herein, the term "prevention" includes either preventing the onset of a clinically evident disease or condition in individuals at risk. Also intended to be encompassed by this definition is the decrease of autophagy in cells to prevent the occurrence of a disease facilitated by autophagy. This includes prophylactic treatment of those having an enhanced risk of developing precancers and cancers facilitated by autophagy. An elevated risk represents an above-average risk that a subject will develop a disease or condition involving autophagy (e.g., cancer), which can be determined, for example, through family history or the detection of genes causing a predisposition to autophagy-dependent disease.

"Pharmaceutically acceptable" as used herein means that the compound or composition is suitable for administration to a subject to achieve the treatments described herein, without unduly deleterious side effects in light of the severity of the disease and necessity of the treatment.

The terms "therapeutically effective" and "pharmacologically effective" are intended to qualify the amount of each agent that will achieve the goal of decreasing disease severity while avoiding adverse side effects such as those typically associated with alternative therapies. The therapeutically effective amount may be administered in one or more doses. An effective amount, on the other hand, is an amount sufficient to provide a significant chemical effect, such as the inhibition of autophagy by a detectable amount.

The term "subject" for purposes of treatment includes any human or animal subject who has a disorder facilitated by autophagy. Such disorders include, but are not limited to cancers and precancers. For methods of prevention the subject is any human or animal subject, and preferably is a human subject who is at risk of acquiring a disorder characterized by unwanted, rapid cell proliferation, such as cancer. The subject may be at risk due to exposure to carcinogenic agents, being genetically predisposed to disorders characterized by unwanted, rapid cell proliferation, and so on. Besides being useful for human treatment, the compounds of the present invention are also useful for veterinary treatment of mammals, including companion animals and farm animals, such as, but not limited to dogs, cats, horses, cows, sheep, and pigs. Preferably, subject means a human.

Autophagy Inhibitors

In one aspect, the present invention provides autophagy inhibiting compounds according to formula I

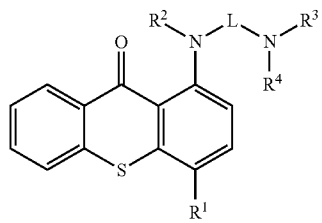

wherein $R^1$ is a group selected from lower alkyl, lower alkyl amide, lower alkyl ester, lower alkyl ketone, and lower alkyl ether; $R^2$ and $R^3$ are H or a group selected from cycloalkyl, lower alkyl, lower alkyl amide, lower alkyl ester, lower alkyl ketone, and lower alkyl ether; $R^4$ is a heteroaryl group; and L is a —$(CH_1)_n$—X—$(CH_2)_n$— group, wherein n is 1, 2, 3, or 4, X is absent, O, S, or N—$R^5$, wherein $R^5$ is H or a lower alkyl group, or a pharmaceutically acceptable salt thereof.

A variety of different embodiments of the invention further specify the nature of the groups present in the formula for the thioxanthenone compounds of formula I. In some embodiments, the heteroaryl group is a quinolinyl, pyridyl, or substituted anthracenyl compound, while in other embodiments the anthracenyl compound is an anthracenyl dione or thioxantheninyl compound. Anthracene diones are substituted or unsubstituted compounds based on the following structure:

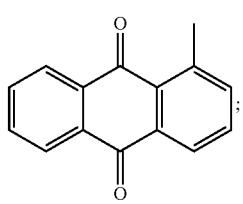 [SMILES: Cc1cccc2c1C(=O)c1ccccc1C2=O]

whereas thioxantheninyl compounds are substituted or unsubstituted compounds based on the following structure:

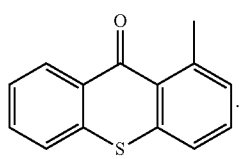 [SMILES: Cc1cccc2sc3ccccc3c(=O)c12]

Any of the various substituents can be any combination or moiety within the ranges or types specified within the claim. For example, in some embodiments, $R^1$ is lower alkyl, while in other embodiments, the linker L is —$CH_2$—$CH_2$—N($CH_3$)—$CH_2$—$CH_2$—.

In further embodiments, the heteroaryl group is selected from the group consisting of:

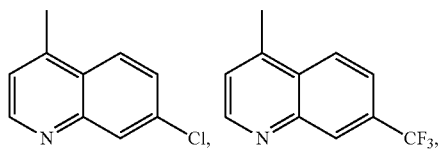

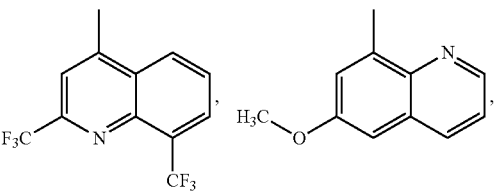

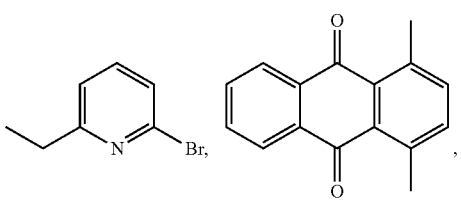

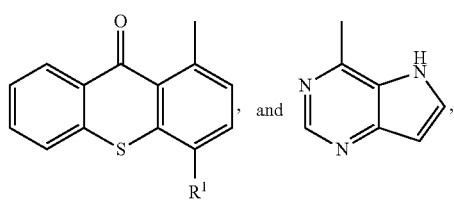

while in yet further embodiments the compound is ROC-325 and has the structure:

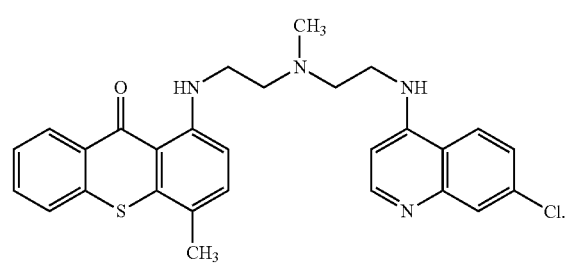 [SMILES: Cc1ccc(NCCN(C)CCNc2ccnc3cc(Cl)ccc23)c2c(=O)c3ccccc3sc12]

In another aspect of the invention, a pharmaceutical composition comprises a compound according to formula I above or as otherwise described herein in combination with a pharmaceutically acceptable carrier, additive or excipient.

Treatment of Diseases and Conditions using Autophagy Inhibitors

A further aspect of the invention provides a method of treating a disease or condition that responds favorably to autophagy inhibition in a subject in need thereof by administering a therapeutically effective amount of a compound of Formula I:

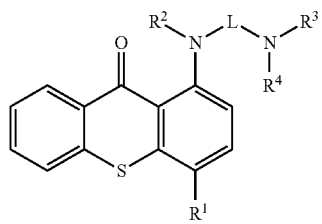

I wherein $R^1$ is a group selected from lower alkyl, lower alkyl amide, lower alkyl ester, lower alkyl ketone, and lower alkyl ether; $R^2$ and $R^3$ are H or a group selected from cycloalkyl, lower alkyl, lower alkyl amide, lower alkyl ester, lower alkyl ketone, and lower alkyl ether; $R^4$ is a heteroaryl group; and L is a —$(CH_2)_n$—X—$(CH_2)_n$— group, wherein n is 1, 2, 3, or 4, X is absent, O, S, or N—$R^5$, wherein $R^5$ is H or a lower alkyl group, or a pharmaceutically acceptable salt thereof. The method also encompasses embodiments including the use of any of the subsets of autophagy inhibitors described herein.

Autophagy is a type II programmed cell death and can initiate cell death in different circumstances. While autophagy plays an important and helpful role in many cells, in some cases it can result in undesirable damage. This damaging autophagic response have been attributed to many diseases and disorders such as neurodegenerative diseases (Fuchs Y, Steller H., Cell 2011; 147: 742-58), cancer, liver diseases (Hidvegi et al., Science 2010; 329: 229-32), cardiac diseases (Thapalia et al., Int J Clin Exp Pathol. 2014; 7(12):8322-41), metabolic syndromes (Codogno et al., Cell Metab 2010; 11: 449-51), diabetes (Pareek et al., Curr Med Res Opin 2014; 30: 1257-66), parasitic infection, aging (Rubinsztein et al., Cell 2011; 146: 682-95), and inflammation (Virgin H W, Levine B. Nat Immunol 2009; 10: 461-70).

A disease or condition that responds favorably to autophagy inhibition is a disease in which autophagy facilitates the progression of the disease or condition, and which is therefore treated by inhibiting autophagy. Examples of diseases or conditions which benefit from the inhibition of autophagy include cancer, diabetes, malaria, schistosomiasis, rheumatoid arthritis, antiphospolipid antibody syndrome, lupus, chronic urticaria, Sjogren's disease, reperfusion injury, and neurodegenerative diseases such as Huntington's disease, Alzheimer's disease, Parkinson's disease, and amyotrophic lateral sclerosis.

In some embodiments, the disease being treated is cancer. Cancer is a disease of abnormal and excessive cell proliferation. Cancer is generally initiated by an environmental insult, certain gene mutations or gene deletions, or error in replication that allows a small fraction of cells to escape the normal controls on proliferation and increase their number. The damage or error generally affects the DNA encoding cell cycle checkpoint controls, or related aspects of cell growth control such as tumor suppressor genes. As this fraction of cells proliferates, additional genetic variants may be generated, and if they provide growth advantages, will be selected in an evolutionary fashion. Cells that have developed growth advantages but have not yet become fully cancerous are referred to as precancerous cells. Cancer results in an increased number of malignant cells in a subject. These cells may form an abnormal mass of cells called a tumor, the cells of which are referred to as tumor cells. The overall amount of tumor cells in the body of a subject is referred to as the tumor load. Tumors can be either benign or malignant. A benign tumor contains cells that are proliferating but remain at a specific site and are often encapsulated. The cells of a malignant tumor, on the other hand, can invade and destroy nearby tissue and spread to other parts of the body through a process referred to as metastasis.

Cancer is generally named based on its tissue of origin. There are several main types of cancer. Carcinoma is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue such as the bone marrow, and causes large numbers of abnormal blood cells to be produced and enter the bloodstream. Lymphoma and multiple myeloma are cancers that begin in the cells of the immune system.

Examples of types of cancer that can be treated using the compounds of the present invention include cancer is selected from the group consisting carcinomas (e.g., squamous-cell carcinomas, adenocarcinomas, hepatocellular carcinomas, and renal cell carcinomas), particularly those of the bladder, bone, bowel, breast, cervix, colon (colorectal), esophagus, head, kidney, liver, lung, nasopharyngeal, neck, ovary, pancreas, prostate, and stomach; leukemias, such as acute myclogenous leukemia, acute lymphocytic leukemia, acute promyelocytic leukemia (APL), acute T-cell lymphoblastic leukemia, adult T-cell leukemia, basophilic leukemia, eosinophilic leukemia, granulocytic leukemia, hairy cell leukemia, leukopenic leukemia, lymphatic leukemia, lynphoblastic leukemia, lymphocytic leukemia, megakaryocytic leukemia, micromyeloblastic leukemia, monocytic leukemia, neutrophilic leukemia and stem cell leukemia; benign and malignant lymphomas, particularly Burkitt's lymphoma, Non-Hodgkin's lymphoma and B-cell lymphoma; benign and malignant melanomas; myeloproliferative diseases; sarcomas, particularly Ewing's sarcoma, hemangiosarcoma, Kaposi's sarcoma, liposarcoma, myosarcomas, peripheral neuroepithelioma, and synovial sarcoma; tumors of the central nervous system (e.g., gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas); germ-line tumors (e.g., bowel cancer, breast cancer, prostate cancer, cervical cancer, uterine cancer, lung cancer (e.g., small cell lung cancer, mixed small cell and non-small cell cancer, pleural mesothelioma, including metastatic pleural mnesothelioma small cell lung cancer and non-small cell lung cancer), ovarian cancer, testicular cancer, thyroid cancer, astrocytoma, esophageal cancer, pancreatic cancer, stomach cancer, liver cancer, colon cancer, and melanoma; mixed types of neoplasias, particularly carcinosarcoma and Hodgkin's disease; and tumors of mixed origin, such as Wilms' tumor and teratocarcinomas, among others. Certain epithelial tumors including ovarian, breast, colon, head and neck, medulloblastoma and B-cell lymphoma, among others are shown to exhibit increased autophagy and are principal target cancers for the autophagy inhibitors of the present invention in some embodiments, while in other embodiments the cancer is leukemia or acute myeloid leukemia.

The effectiveness of cancer treatment may be measured by evaluating a reduction in tumor load or decrease in tumor growth in a subject in response to the administration of the ubiquitin-activating agent. The reduction in tumor load may be represent a direct decrease in mass, or it may be measured in terms of tumor growth delay, which is calculated by subtracting the average time for control tumors to grow over to a certain volume from the time required for treated tumors to grow to the same volume.

In some embodiments, the method further comprises administration of an additional anticancer agent. An additional anticancer agent is known anticancer agent that can be co-administered with one or more compounds of the present invention for cancer treatment. Co-administration can either be simultaneous, or proximal in time. Examples of anticancer agents include angiogenesis inhibitors such as angiostatin KI-3, DL-α-difluoromethyl-omithine, endostatin, fumagillin, genistein, minocycline, staurosporine, and (±)-thalidomide; DNA intercalating or cross-linking agents such as bleomycin, carboplatin, carmustine, chlorambucil, cyclophosphamide, cisplatin, phenanthriplatin, meiphalan, mitoxantrone, and oxaliplatin; DNA synthesis inhibitors such as methotrexate, 3-Amino-1,2,4-henzotriazine 1,4-dioxide, aminopterin, cytosine β-D-arabinofuranoside, 5-Fluoro-5'-deoxyuridine, S-Fluorouracil, gaciclovir, hydroxyurea, and mitomycin C; DNA-RNA transcription regulators such as actinomycin D, daunorubicin, doxorubicin, homoharringtonine, and idarubicin; enzyme inhibitors such as S(+)-camptothecin, curcumin, (−)-deguelin, 5,6-dichlorobenz-imidazole 1-β-D-ribofuranoside, etoposine, formestane, fistriecin, hispidin, cyclocreatine, mevinolin, trichostatin A, tyrophostin AG 34, and tyrophostin AG 879, Gene Regulating agents such as 5-aza-2'-deoxycitidine, azacitidine, decitabine, cholecalciferol, 4-hydroxytamoxifen, melatonin, mifepristone, raloxifene, all trans-retinal, all trans retinoic acid, 9-cis-retinoic acid, retinol, tamoxifen, and troglitazone; Microtubule Inhibitors such as colchicine, dolostatin 15, nocodazole, paclitaxel, podophyllotoxin, rhizoxin, vinblastine, vincristine, vindesine, and vinorelbine; and various other antitumor agents such as 17-(allylamino)-17-demethoxygeldanamycin, 4-Amino-1,8-naphthalimide, apigenin, brefeldin A, cimetidine, dichloromethylene-diphosphonic acid, leuprolide, luteinizing-hormone-releasing hormone, pifithrin-α, rapamycin, thapsigargin, and bikunin, and derivatives thereof.

Candidate agents may be tested in animal models. Typically, the animal model is one for the study of cancer. The study of various cancers in animal models (for instance, mice) is a commonly accepted practice for the study of human cancers. For instance, the nude mouse model, where human tumor cells are injected into the animal, is commonly accepted as a general model useful for the study of a wide variety of cancers (see, for instance, Polin et al., Investig. New Drugs, 15:99-108 (1997)). Results are typically compared between control animals treated with candidate agents and the control littermates that received a vehicle that does not contain the test agent. Transgenic animal models are also available and are commonly accepted as models for human disease (see, for instance. Greenberg et al., Proc. Natl. Acad. Sci. USA, 92:3439-3443 (1995)). Candidate agents can be used in these animal models to determine if a candidate agent decreases one or more of the symptoms associated with the cancer, including, for instance, cancer metastasis, cancer cell motility, cancer cell invasiveness, or combinations thereof.

Another aspect of the invention provides a method of inhibiting autophagy in cells of a subject, comprising contacting the cells with an effective amount of a compound according to formula I:

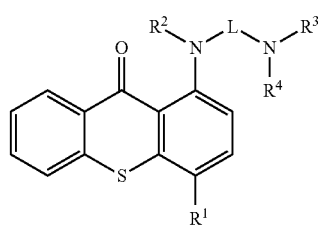

wherein $R^1$ is a group selected from lower alkyl, lower alkyl amide, lower alkyl ester, lower alkyl ketone, and lower alkyl ether; $R^2$ and $R^3$ are H or a group selected from cycloalkyl, lower alkyl, lower alkyl amide, lower alkyl ester, lower alkyl ketone, and lower alkyl ether; $R^4$ is a heteroaryl group; and L is a —$(CH_2)_n$—X—$(CH_2)_n$— group, wherein n is 1, 2, 3, or 4, X is absent, O, S, or N—$R^5$, wherein $R^5$ is H or a lower alkyl group, or a pharmaceutically acceptable salt thereof.

Autophagy is a highly regulated process of biological systems that plays a normal part in cell growth development and homeostasis helping to maintain a balance between the synthesis, degradation, and subsequent recycling of cellular products. It is a major mechanism by which a cell allocates nutrients from unnecessary processes to more-essential processes.

A number of autophagic processes occur in nature, all of which have the degradation of intracellular components via the lysosome as a common feature. A well-known mechanism of autophagy involves the formation of a membrane around a targeted region of a cell, separating the contents from the rest of the cytoplasm. The resultant vesicle then fuses with a lysosome which subsequently degrades the contents.

Autophagy consists of the sequestration of organelles and proteins in autophagic vesicles (AV) and degradation of this cargo through lysosomal fusion. Autophagy allows tumor cells to survive metabolic and therapeutic stresses. Multiple publications by those skilled in the art indicate therapy-induced autophagy is a key resistance mechanism to many anti-cancer agents.

The present invention includes methods of inhibiting autophagy in a cell, particularly the cell of a subject. The methods can be used to inhibit autophagy in a cell in various environments. For example, in some embodiments, the cells are contacted in vivo, while in other embodiments the cells are contacted in vitro or ex vivo. The resulting inhibition of authophagy can be monitored or applied in the cell to evaluate effectiveness of the agent, effect a favorable result such as treatment of a disease or condition involving autophagy, or to study the effect of inhibition of autophagy in the cell.

Administration and Formulation of Autophagy Inhibitors

The present invention also provides pharmaceutical compositions that include autophagy inhibitors according to formula I as an active ingredient, and a pharmaceutically acceptable liquid or solid carrier or carriers, in combination with the active ingredient. Any of the compounds described above as being suitable for the treatment of diseases or conditions that respond favorably to autophagy inhibition can be included in pharmaceutical compositions of the invention.

The autophagy inhibitors can be administered as pharmaceutically acceptable salts. Pharmaceutically acceptable salt refers to the relatively non-toxic, inorganic and organic acid addition salts of the autophagy inhibitors. These salts can be prepared in situ during the final isolation and purification of the autophagy inhibitor, or by separately reacting a purified autophagy inhibitor with a suitable counterion, depending on the nature of the compound, and isolating the salt thus formed. Representative counterions include the chloride, bromide, nitrate, ammonium, sulfate, tosylate, phosphate, tartrate, ethylenediamine, and maleate salts, and the like. See for example Haynes et al., J. Pharm. Sci., 94, p. 2111-2120 (2005).

The pharmaceutical compositions includes one or more autophagy inhibitors together with one or more of a variety of physiological acceptable carriers for delivery to a patient, including a variety of diluents or excipients known to those of ordinary skill in the art. For example, for parenteral administration, isotonic saline is preferred. For topical administration, a cream, including a carrier such as dimethylsulfoxide (DMSO), or other agents typically found in topical creams that do not block or inhibit activity of the peptide, can be used. Other suitable carriers include, but are not limited to, albumin, alcohol, phosphate buffered saline, and other balanced salt solutions.

The formulations may be conveniently presented in unit dosage form and may be prepared by any of the methods well known in the art of pharmacy. Preferably, such methods include the step of bringing the active agent into association with a carrier that constitutes one or more accessory ingredients. In general, the formulations are prepared by uniformly and intimately bringing the active agent into association with a liquid carrier, a finely divided solid carrier, or both, and then, if necessary, shaping the product into the desired formulations. The methods of the invention include administering to a subject, preferably a mammal, and more preferably a human, the composition of the invention in an amount effective to produce the desired effect. The autophagy inhibitors can be administered as a single dose or in multiple doses. Useful dosages of the active agents can be determined by comparing their in vitro activity and the in vivo activity in animal models. Methods for extrapolation of effective dosages in mice, and other animals, to humans are known in the art; for example, see U.S. Pat. No. 4,938,949.

The agents of the present invention are preferably formulated in pharmaceutical compositions and then, in accordance with the methods of the invention, administered to a subject, such as a human patient, in a variety of forms adapted to the chosen mute of administration. The formulations include, but are not limited to, those suitable for oral, rectal, vaginal, topical, nasal, ophthalmic, or parental (including subcutaneous, intramuscular, intraperitoneal, intratumoral, and intravenous) administration.

Formulations of the present invention suitable for oral administration may be presented as discrete units such as tablets, troches, capsules, lozenges, wafers, or cachets, each containing a predetermined amount of the active agent as a powder or granules, as liposomes containing the celecoxib derivatives, or as a solution or suspension in an aqueous liquor or non-aqueous liquid such as a syrup, an elixir, an emulsion, or a draught. Such compositions and preparations typically contain at least about 0.1 wt-% of the active agent. The amount of autophagy inhibitor (i.e., active agent) is such that the dosage level will be effective to produce the desired result in the subject.

Nasal spray formulations include purified aqueous solutions of the active agent with preservative agents and isotonic agents. Such formulations are preferably adjusted to a pH and isotonic state compatible with the nasal mucous membranes. Formulations for rectal or vaginal administration may be presented as a suppository with a suitable carrier such as cocoa butter, or hydrogenated fats or hydrogenated fatty carboxylic acids. Ophthalmic formulations are prepared by a similar method to the nasal spray, except that the pH and isotonic factors are preferably adjusted to match that of the eye. Topical formulations include the active agent dissolved or suspended in one or more media such as mineral oil, petroleum, polyhydroxy alcohols, or other bases used for topical pharmaceutical formulations.

The tablets, troches, pills, capsules, and the like may also contain one or more of the following: a binder such as gum tragacanth, acacia, corn starch or gelatin; an excipient such as dicalcium phosphate; a disintegrating agent such as corn starch, potato starch, alginic acid, and the like; a lubricant such as magnesium stearate; a sweetening agent such as sucrose, fructose, lactose, or aspartame; and a natural or artificial flavoring agent. When the unit dosage form is a capsule, it may further contain a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, sugar, and the like. A syrup or elixir may contain one or more of a sweetening agent, a preservative such as methyl- or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The active agent may be incorporated into sustained-release preparations and devices.

Preparation of the Compounds

Compounds of the invention may be synthesized by synthetic routes that include processes similar to those well known in the chemical arts, particularly in light of the description contained herein. The starting materials are generally available from commercial sources such as Aldrich Chemicals (Milwaukee, Wis., USA) or are readily prepared using methods well known to those skilled in the art (e.g., prepared by methods generally described in Louis F. Fieser and Mary Fieser. *Reagents for Organic Synthesis*, v. 1-19, Wiley, New York, (1967-1999 ed.); Alan R. Katritsky, Otto Meth-Cohn, Charles W. Rees, *Comprehensive Organic Functional Group Transformations*, v 1-6, Pergamon Press, Oxford, England, (1995); Barry M. Trost and Ian Fleming, *Comprehensive Organic Synthesis*, v. 1-8. Pergamon Press, Oxford, England, (1991); or *Beilsteins Handbuch der organischen Chemie*, 4, Aufl. Ed. Springer-Verlag, Berlin, Germany, including supplements (also available via the Beilstein online database)).

Those skilled in the art will appreciate that other synthetic routes may be used to synthesize the compounds of the invention. Although specific starting materials and reagents are depicted in the reaction schemes and discussed below, other starting materials and reagents can be easily substituted to provide a variety of derivatives and/or reaction conditions. In addition, many of the compounds prepared by the methods described below can be further modified in light of this disclosure using conventional methods well known to those skilled in the art.

The present invention is illustrated by the following examples. It is to be understood that the particular examples, materials, amounts, and procedures are to be interpreted broadly in accordance with the scope and spirit of the invention as set forth herein.

EXAMPLES

Example 1

ROC-325: A Novel Inhibitor of Autophagy with Single Agent In Vivo Anticancer Activity Autophagy is an evolutionarily conserved mechanism of lysosomal proteolysis that is used for the turnover of organelles and proteins with long half-lives and also functions to generate alternative sources of metabolic fuel via nutrient recycling under stress conditions. Although multiple key studies have demonstrated that autophagy functions as mechanism of tumor suppression via the elimination of defective pre-malignant cells, overwhelming evidence supports a major role for autophagic degradation in the maintenance of bioenergetic homeostasis under stress conditions including hypoxia and nutrient deprivation.

Autophagy has also emerged as an important mechanism of resistance to radiation, classical chemotherapy, and targeted anticancer agents due to its ability to augment the survival capacity of malignant cells. Carew et al., Cancer management and research 2012; 4:357-65. Carew et al., Autophagy 2007; 3:464-7. The data supporting roles for autophagy as a mediator of drug resistance and malignant progression provided a logical foundation to devise strategies to impair this process for therapeutic benefit. Chloroquine (CQ) and hydroxychloroquine (HCQ) have been used for decades to treat malaria, rheumatoid arthritis, and lupus and represent two of a very small group of FDA-approved drugs that disrupt lysosomal function and consequently inhibit autophagy. These specific properties of CQ/HCQ spurred numerous preclinical investigations focused on establishing the safety and therapeutic benefit of inhibiting autophagy to increase the efficacy of a diverse range of anticancer agents. Based on the positive impact of HCQ in this scenario, a series of phase I and phase I/II trials were initiated to investigate the safety and preliminary efficacy of the addition of HCQ to existing anticancer regimens. The findings from the first six of these trials were co-published last year. Rangwala et al., Autophagy 2014; 10:1391-402; Vogle al., Autophagy 2014; 10:1380-90; Rangwala et al., Autophagy 2014; 10:1369-79; Mahalingam et al., Autophagy 2014; 10:1403-14; Rosenfeld et al., Autophagy 2014; 10:1359-68; Barnard et al., Autophagy 2014; 10:1415-25. Although the addition of HCQ was generally safe and preliminary efficacy was observed in a minority of patients treated with HCQ-based regimens, it was unclear if the maximum tolerated dose (MTD) of HCQ in these studies resulted in complete autophagic inhibition.

The results of the initial clinical studies of HCQ-based combination regimens underscored the need for better agents to antagonize autophagic degradation. However, no comprehensive structure activity relationship (SAR) analyses on CQ/HCQ had been conducted to date and it was therefore unclear which specific structural modifications to these agents may result in increased anti-autophagic potency or efficacy. The inventors used logical medicinal chemistry approaches to generate a series of new compounds containing modified core elements of HCQ and other agents that have previously been reported to inhibit autophagy and tested their autophagic inhibition and in vitro anticancer activity to identify a lead compound. ROC-325 inhibits autophagy at significantly lower doses and exhibits significantly superior single agent anticancer activity against a broad range of tumor types compared to HCQ. Focused studies in models of renal cell carinoma (RCC) demonstrated that ROC-325 treatment led to the deacidification of lysosomes, accumulation of autophagosomes, and disrupted autophagic flux. Oral administration of ROC-325 to mice bearing RCC xenografts was well tolerated and yielded dose-dependent inhibition of tumor growth that was significantly more efficacious than a higher dose of HCQ. Analysis of tumor specimens from mice treated with ROC-325 demonstrated in vivo autophagy inhibition, reduced tumor cell proliferation, and apoptosis. The findings establish the foundation for further investigation of ROC-325 as a novel agent for autophagy-dependent malignancies and other disorders where lysosomal activity contributes to disease pathogenesis.

Materials & Methods

Synthesis of ROC-325.

Cells and cell culture. A498, 786-0, Achn and Caki-2 cells were obtained from ATCC (Manassas. Va.). Cells were cultured with medium supplemented with 10% FBS at 37° C. with 5% $CO_2$ as previously described. Swords et al., Blood 2010; 115:3796.800. Human normal renal proximal tubule epithelial cells (RPTEC) were purchased from Clonetics (Walkersville, Md.) and cultured in REGM media (REGM BulletKit, Clonetics). Cell lines were authenticated by the source banks using DNA profiling techniques and were used for this study in accordance with AACR guidelines.

Chemicals and reagents. Reagents were obtained from the following sources: giemsa stain, acridine orange, bafilomycin A1, propidium iodide, 3-(4,5-dimethylthiazol-2-yl)-2,5-diphenyltetrazolium bromide (MTT), hydroxychloroquine, and anti-pt tubulin antibody (Sigma, St. Louis, Mo.), anti-active caspase-3 (Cell Signaling, Beverly, Mass.), anti-LC3B and anti-p62 (Abcam, Cambridge, Mass.), anti-cathepsin D (Santa Cruz Biotech, Santa Cruz. Calif.), goat anti-rabbit horseradish peroxidase (HRP)-conjugated secondary antibody (Jackson Laboratories, West Grove, Pa.), sheep anti-mouse-HRP and donkey anti-rabbit-HRP (Amersham. Pittsburgh, Pa.).

Transmission electron microscopy. Transmission electron microscopy of cells was performed as previously described. Carew et al., J Cell Mol Med 2010 Oct.; 14(10):2448-59. RCC cells were treated with ROC-325 for 24 h and harvested for imaging. Briefly, sections were cut in an LKB Ultracut microtome (Leica. Deerfield, Ill.), stained with uranyl acetate and lead citrate, and examined in a JEM 1230 transmission electron microscope (JEOL, USA, Inc., Peabody, Mass.). Images were captured using the AMT Imaging System (Advanced Microscopy Techniques Corp, Danvers. Mass.).

Giemsa staining. Cells were plated in chamber slides as previously described and treated with ROC-325 for 24 h. Carew et al., J Biol Chem 2011; 286:6602-13. Following drug treatment, cells were washed with PBS and fixed in methanol for 5 minutes. Cells were then incubated for 1 h in Giemsa stain diluted 1:20 with deionized water. Cells were rinsed with water and imaged using an Olympus fluorescent microscope. Image-Pro Plus software Version 6.2.1 was used for image acquisition.

Acridine orange staining. Acidic lysosomes were visualized by acridine orange staining as previously described. Carew et al., J Biol Chem 2011; 286:6602-13. After treatment with ROC-325 for 24 h, cells were stained with 1 μM acridine orange for 15 minutes at 37° C. Cells were washed with PBS and images were captured using an Olympus fluorescent microscope. Acidic lysosomes appear as orange fluorescent cytoplasmic vesicles. Quantification of 5 random fields of acridine orange intensity and image acquisition were performed using Image-Pro Plus software Version 6.2.1.

Immunocytochemistry. Cells were plated on chamber slides and allowed to attach overnight. Cells were then treated for 24 h with ROC-325. Following drug treatment, cells were fixed with 4% paraformaldehyde, permeabilized using 0.2% triton-X-100, and incubated overnight with anti-LC3B antibody. Alexa Fluor 594 conjugated fluorescent secondary antibody was used to visualize protein localization. Dapi was utilized to stain the nucleus. Images were captured using an Olympus fluorescent microscope (Center Valley, Pa.) with a DP71 camera and a 60× objective. Image-Pro Plus software Version 6.2.1 (MediaCybernetics, Bethesda, Md.) was used for image acquisition.

Expression microarrays. RCC cells were treated with ROC-32 for 24 h. Total RNAs were isolated using the RNeasy Plus Mini Kit (Qiagen, Germantown, Md.) and treated with TURBO DNA-Free™ Kit (Applied Biosystems, Foster City, Calif.), 300 ng of total RNA per sample was amplified and hybridized to GeneChip® Human Gene 1.0 ST arrays (Affymetrix, Inc., Santa Clara, Calif.) according to the manufacturer's instructions. Affymetrix CEL files were imported into Partek® Genomics Suite™ 6.4 (Partek Inc., St. Louis. Mo.) using the default Partek normalization parameters and the robust multi-array average (RMA) analysis adjusted for probe sequence and GC content (GC-RMA). Data normalization was performed across all arrays using quantile normalization.

Quantitative real time polymerase chain reaction, cDNA from ROC-325 treated cells were used for relative quantification by RT-PCR analyses. First-strand cDNA synthesis was performed from 1 μg RNA in a 20 μl reaction mixture using the high-capacity eDNA Reverse Transcription Kit (Applied Biosystems, Foster City, Calif.). Cathepsin D (CTSD) and GAPDH transcripts were amplified using commercially available TaqMan® Gene expression assays (Applied Biosystems, Foster City, Calif.). Relative gene expression was calculated with the 2-Ct method using GAPDH as a housekeeping gene. Pfaffl M W., Nucleic Acids Res 2001; 29:e45.

Quantification of drug-induced cytotoxicity. Cell viability was assessed by MIT assay. Cells were seeded into 96-well microculture plates at 10,000K cells per well and allowed to attach for 24 h. Cells were then treated with ROC-325 or HCQ for 72 h. Following drug treatment, MTT was added and cell viability was quantified using a BioTek (Winooski, Vt.) microplate reader. Pro-apoptotic effects following in vitro drug exposure were quantified by propidium iodide (PI) staining and fluorescence-activated cell sorting (FACS) analysis of sub-G0/G1 DNA content as previously described and by measurement of active caspase-3 by flow cytometry using a commercial kit (BD Biosciences, San Jose, Calif.). Mahalingam et al., Clin Cancer Res 2010; 16:141-53.

Immunoblotting. Renal cancer cells were incubated with ROC-325 for 24 h. Cells were harvested and were then lysed as previously described. Nawrocki S T, Carew J S, Maclean K H, Courage J F, Huang P, Houghton J A, Cleveland J L, Giles F J, McConkey D J. Myc regulates aggresome formation, the induction of Noxa, and apoptosis in response to the combination of bortezomib and SAHA. Blood 2008; 112: 2917-26. Approximately 50 μg of total cellular protein from each sample were subjected to SDS-PAGE, proteins were transferred to nitrocellulose membranes, and the membranes were blocked with 5% nonfat milk in a Tris-buffered saline solution containing 0.1% Tween-20 for 1 h. The blots were then probed overnight at 4° C. with primary antibodies, washed, and probed with species-specific secondary antibodies coupled to horseradish peroxidase. Immunoreactive material was detected by enhanced chemiluminescence (West Pico, Pierce, Inc., Rockville. Ill.).

In vivo evaluation of ROC-325 and HCQ. 786-O renal cancer cells (5×106) were suspended in a mixture of HBSS and Matrigel and subcutaneously implanted into female nude mice (BALB/c background). Tumor-bearing animals from each cell line xenograft were randomized into treatment groups. Mice were treated with vehicle (water), ROC-325 (25, 40, and 50 mg/kg PO), or HCQ (60 mg/kg IP) QD×5 for 6 weeks. Mice were monitored daily and tumor volumes were measured twice weekly. At study completion, tumors from representative animals were excised from each group, formalin-mixed, and paraffin-embedded for immunohistochemical analysis.

Immunohistochemistry. Paraffin-embedded tumor sections were deparaffinized in xylene, exposed to a graded series of alcohol, and rehydrated in PBS (pH 7.5). Heat-induced epitope retrieval on paraffin-embedded sections and probing with specific antibodies was conducted as previously described. Nawrocki et al., Clin Cancer Res 2013; 19:3577-90. Positive reactions were visualized using 3,3'-diaminobenzidine (Dako, Glostrup, Denmark). Images were captured using an Olympus fluorescent microscope (Center Valley. Pa.) with a DP71 camera and a 20× objective. Image-Pro Plus software Version 6.2.1 (MediaCybernetics, Bethesda, Md.) was used for image acquisition. ImageJ software was used for quantification of LC3B and p62 levels by densitometric analysis of five random fields containing viable tumor cells. Quantification of cleaved caspase-3 was conducted by counting the number of positive cells in five random fields as previously described. Carew et al., Cancer Res 2008; 68:4783-90.

Statistical analyses. Statistical significance of differences observed between samples was determined using the Student's t test. Differences were considered significant in all experiments at $p<0.05$ with two-sided comparisons.

Results

Figure 1:
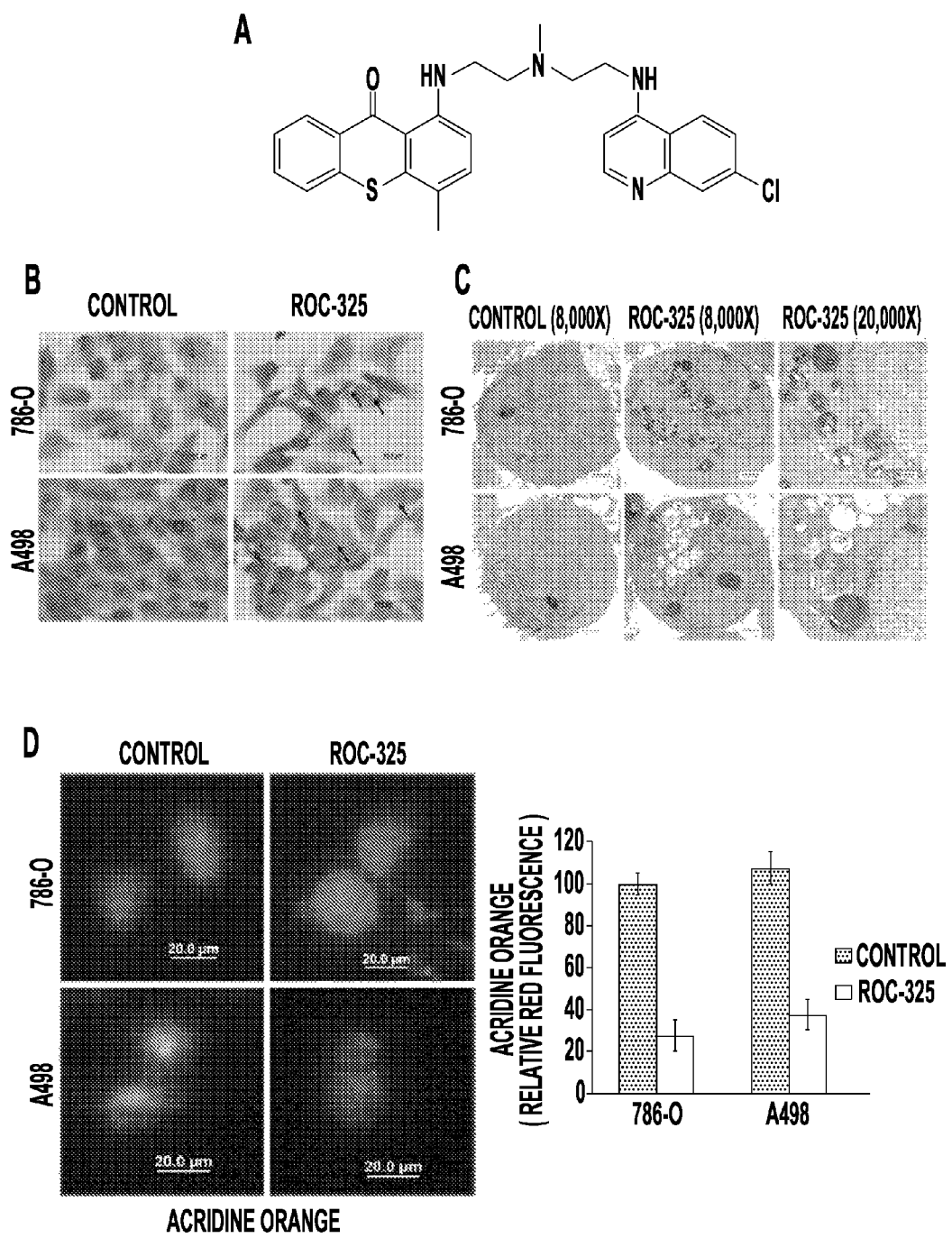
FIG. 1 (A-D) provides graphs and images showing ROC-325 induced vacuolization and lysosome membrane permeability. A) Chemical structure of ROC-325; B) ROC-325 induces vacuolization. 786-O and A498 cells were treated for 24 h with 5 μM ROC-325. Cell morphology and vacuolization were visualized by Giemsa staining; C) Electron microscopy demonstrates vacuolization and electron dense particle accumulation. Cells were treated with 5 μM ROC-325 for 24 h. Cells were fixed and prepared for electron microscopy; D) Measurement of lysosome membrane permeability by loss of acridine orange fluorescence. Red acridine orange staining was measured in 786-O and A498 cells by immunofluorescence and quantified using ImageJ software. Mean±SD, n=5. *Indicates a significant difference from the controls. P<0.05.

ROC-325 induces lysosomal deacdification and autophagosome formation. In order to develop new agents with both improved autophagic inhibition and single agent anticancer activity, the inventors created a series of compounds that contained motifs of HCQ, lucanthone (LUC), and other known autophagy inhibitors. In order to identify a lead compound for further development, the inventors first stratified based on the ability of their new agents to reduce the viability of malignant cells and increase the expression of p62, a protein that is known to be specifically turned over by autophagy. Bjorkoy et al., J Cell Biol 2005; 171:603-14. Based on these initial assays, ROC-325 was identified as a lead agent (FIG. 1A). Direct comparison of the in vitro anticancer effects of ROC-325 and HCQ in 12 different human cancer cell lines with diverse genetic backgrounds demonstrated that ROC-325 possessed significantly lower $IC_{50}$s (approximately 10-fold) than HCQ in all models tested (Table 1). RCC was selected as a specific tumor type for further investigation of the pharmacological properties of ROC-325 based on the sensitivity of A498 cells in these preliminary screens and clinical efficacy previously observed in a patient with RCC treated with a combination of HCQ and vorinostat after failing seven lines of prior therapy in the inventors' recent investigator-initiated clinical trial. Mahalingam et al., Autophagy 2014; 10:1403-14. Giemsa staining of A498 and 786-O cells demonstrated that ROC-325 induced cytosolic vacuolization (FIG. 1B). Transmission electron microscopy analyses showed that it promoted the accumulation of autophagosomes (FIG. 1C). Treatment with ROC-325 also resulted in a significant loss of acridine orange fluorescence, which is consistent with an increase in lysosomal membrane permeability (LMP) and the consequential deacidification of lysosomes (FIG. 1D). These collective findings demonstrated that the chemical refinements of the HCQ core motifs that were included to produce ROC-325 resulted in significantly greater anticancer while retaining lysosomal disrupting properties.

TABLE 1

$IC_{50}$ values from 72 h MTT assays.

| Cell line | Tumor Type | ROC-325 $IC_{50}$ (μM) | HCQ $IC_{50}$ (μM) |
|---|---|---|---|
| A498 | Renal | 4.9 | 52 |
| A549 | Lung | 11 | >75 |
| CFPAC-1 | Pancreas | 4.6 | >75 |
| COLO-205 | Colon | 5.4 | 51 |
| DLD-1 | Colon | 7.4 | >75 |
| IGROV-1 | Ovarian | 11 | >75 |
| MCF-7 | Breast | 8.2 | >75 |
| MiaPaCa-2 | Pancreas | 5.8 | >75 |
| NCI-H69 | Lung | 5.0 | 54 |
| PC-3 | Prostate | 11 | 58 |
| RL | NHL | 8.4 | 35 |
| UACC-62 | Melanoma | 6.0 | >75 |

Figure 2:
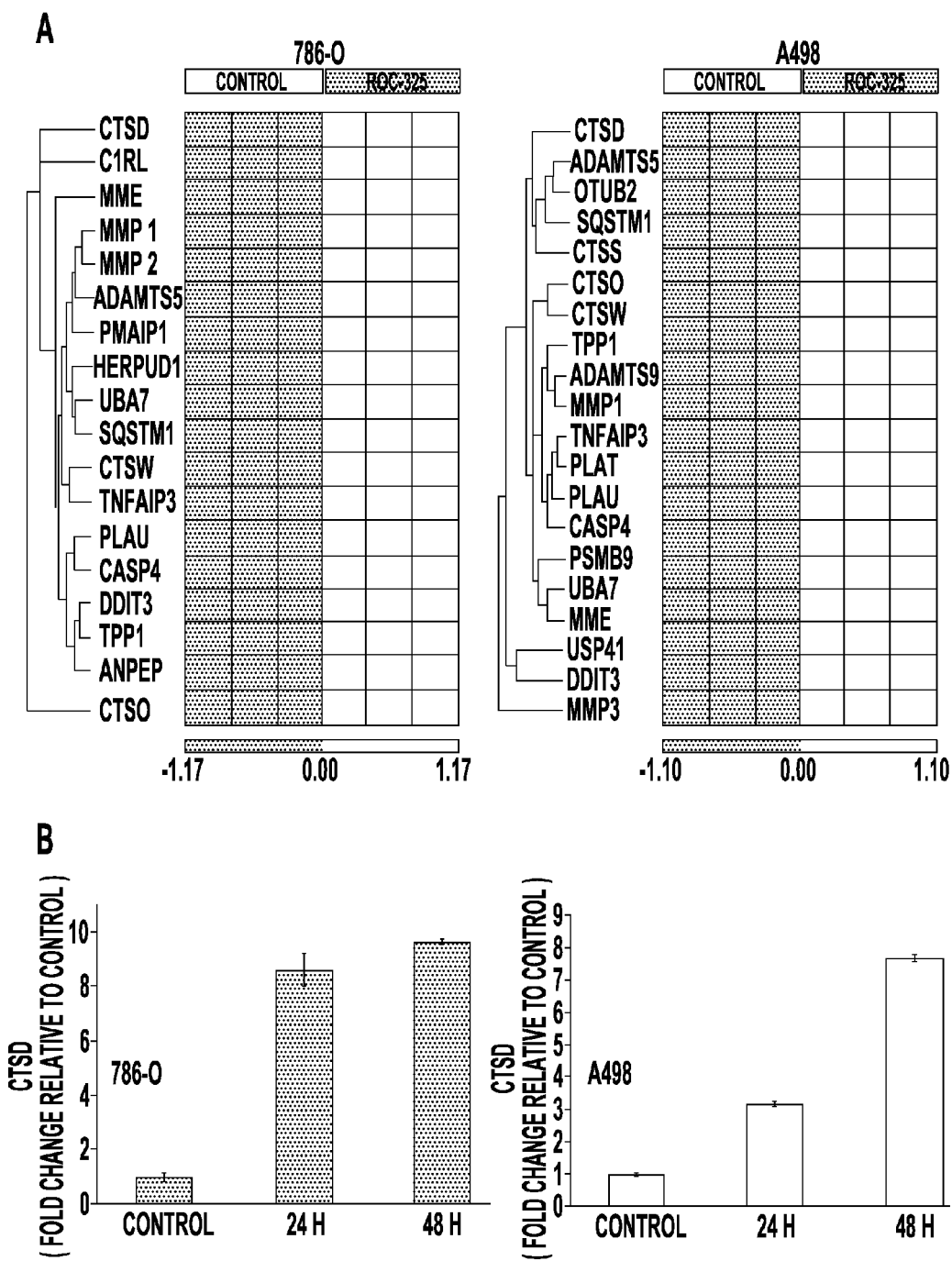
FIG. 2 (A, B) provides graphs showing cathepsin D expression is highly induced following ROC-325 treatment. A) Affymetrix expression arrays identify cathepsin D (CTSD) as a strongly upregulated gene in both 786-O and A498 renal cell carcinoma (RCC) cells. Cells were treated with 5 μM ROC-325 for 24 h. RNA isolation and expression arrays were performed as described in the Materials and Methods. Heat maps represent proteolysis genes significantly upregulated following ROC-325 treatment; B) Quantitative real-time PCR analysis of cathepsin D expression in 786-O and A498 RCC cells. Cells were treated with 5 μM ROC-325 for 24 and 48 h and then harvested for analysis. Levels of mRNAs were standardized to the expression of GAPDH. Mean±SD, n=3.

ROC-325 triggers cathepsin D expression. The inventors previously showed that CQ/CQ and lucanthone (LUC) induce the increased expression of the lysosomal protease cathepsin D (CTSD). Carew et al., Blood 2007; 110:313-22. Carew et al., J Cell Mol Med 2010; 14:2448-59. The LMP-related effects of HCQ and LUC also promote its subcellular relocalization from lysosomal compartments into the cytosol. Notably, in direct contrast to the majority of lysosomal proteases that require a strict acidic pH environment for their activity, CTSD retains proteolytic function under cytosolic conditions and has been shown to play an active role in apoptosis when relocalized to the cytosol. Beaujouin et al., Oncogene 2006; 25:1967-73; Haendeler et al., J Biol Chem 2005; 280:42945-51; Liaudet-Coopman et al., Cancer Lett 2006; 237:167-79. Indeed, earlier work by the inventors showed that the pro-apoptotic effects of CQ and LUC in malignant cells were significantly impaired when CTSD was targeted using RNAi approaches. Microarray analyses were conducted to assess the global effects of ROC-325 on the gene expression profiles of RCC cells. A498 and 786-0 were treated with 5 μM ROC-325 for 24 hours and subjected to Affymetrix microarray quantification of pharmacodynamic changes in gene expression. Heat map analyses identified significant upregulation of genes involved with proteolysis in each cell line (FIG. 2A). Similar to the autophagy inhibitors CQ/HCQ and LUC, ROC-325 triggered a highly significant increase in CTSD levels, which were confirmed by qRT-PCR (FIG. 2B). In addition to this specific effect, ROC-325 treatment also stimulated the expression of other genes with important roles in the control of protein turnover and ER stress-induced apoptosis including UBA7, TNFA1P1, DD1T3, PMA1P1, and CASP4 indicating a link between the induction of apoptosis and the disruption of protein homeostasis.

Figure 3:
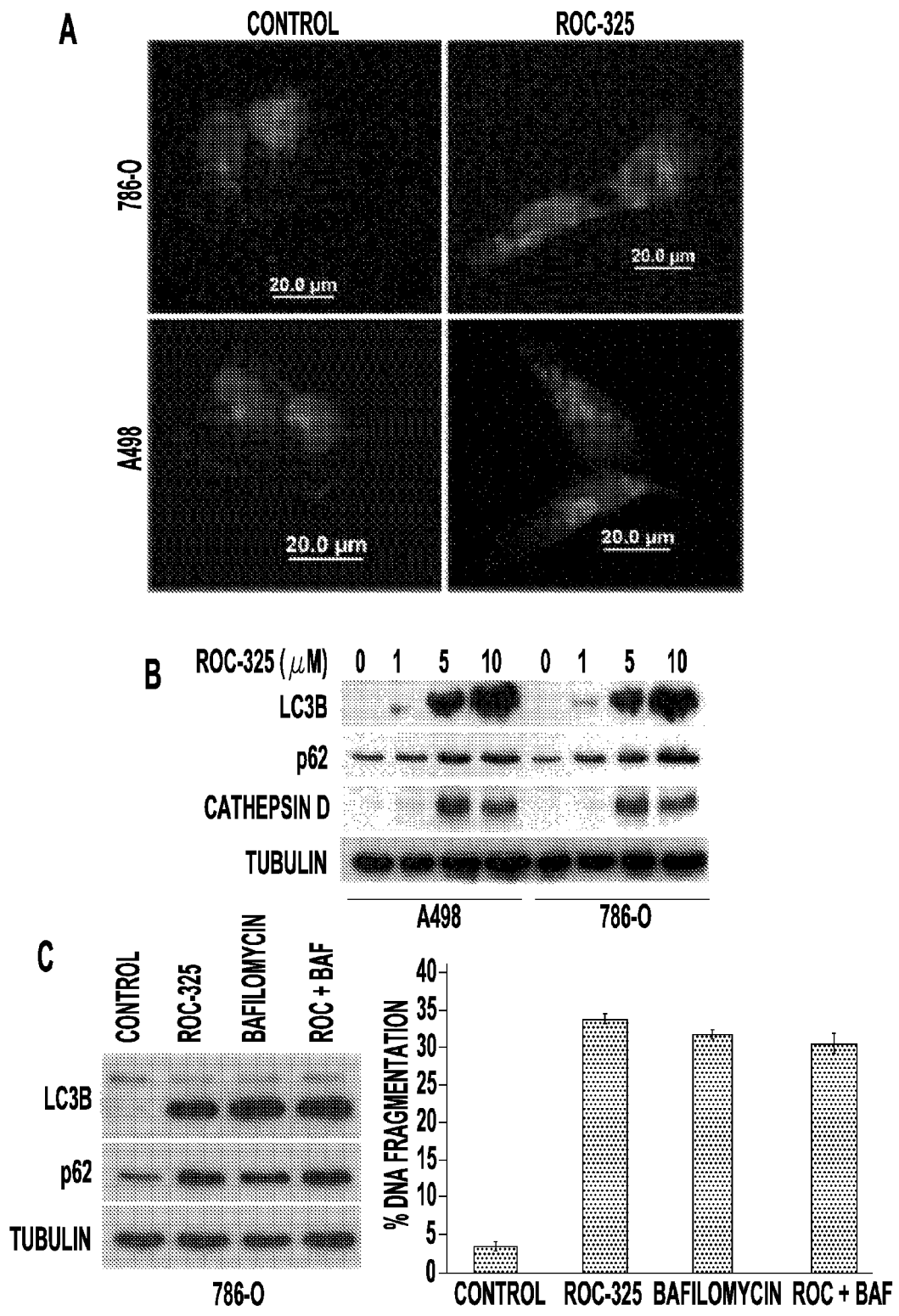
FIG. 3 (A-C) provides graphs and images showing ROC-325 inhibits autophagy. A) ROC-325 induces LC3B accumulation. RCC cells were treated with 5 μM ROC-325 for 24 h, LC3B accumulation was visualized by immunocytochemistry; B) ROC-325 increases LC3B, p62, and cathepsin D expression. 786-O and A498 cells were treated with the indicated concentrations of ROC-325 for 24 h. Protein levels were determined by immunoblotting; C) Bafilomycin A1 does not augment ROC-325-mediated LC3B or p62 accumulation or apoptosis. 786-O cells were treated with 5 μM ROC-325, 100 nM bafilomycin A1, or both agents for 48 h. Protein expression was determined by immunoblotting and apoptosis by PI-FACS analysis. Mean±SD, n=3.

ROC-325 induces hallmarks of autophagy inhibition and antagonizes autophagic flux. The morphological and gene expression analyses in RCC cells indicated that ROC-325 treatment yielded pharmacodynamic effects that were consistent with inhibition of autophagy. In order to further investigate the specific effects of ROC-325 on autophagy, the inventors first utilized fluorescent confocal microscopy to quantify the impact of drug treatment on LC3B distribution. Treatment with 5 μM ROC-325 for 24 hours led to the formation of LC3B punctae and a robust increase in LC3B levels in both A498 and 786-0 RCC cells (FIG. 3A). Immunoblotting analyses conducted in both A498 and 786-0 cells demonstrated that ROC-325 promoted a dose-dependent increase in LC3B expression in manner that correlated with a corresponding increase in the levels of p62, and cathepsin D (FIG. 3B). The autophagy inhibitor bafilomycin A1 was used next as a tool to evaluate the effects of ROC-325 on autophagic flux. 786-0 cells were treated with ROC-325 alone and in combination with bafilomycin A1 and the levels of LC3B and p62 were quantified by immunoblotting. No significant differences in the levels of either LC3B or p62 were detected when ROC-325 was combined with bafilomycin A1 thus indicating that ROC-325 effectively inhibited autophagic flux (FIG. 3C). Furthermore, the addition of batilomycin A1 did not significantly augment the ability of ROC-325 to induce apoptosis (FIG. 3C). The results collectively demonstrate that ROC-325 disrupts autophagic degradation.

ROC-325 exhibits therapeutic selectivity and has significantly greater anticancer activity than HCQ. The inventors next treated four different RCC cell lines (786-0, A498, Achn, and Caki-2) with a range of concentrations of ROC-325 and HCQ for 72 hours. The effects of each agent on cell viability were determined by MTT assay. A direct comparison of the activity of ROC-325 and HCQ revealed that ROC-325 was approximately 10-fold more effective at diminishing RCC cell viability than HCQ (FIG. 4A). In order to determine the in vitro selectivity of ROC-325 for malignant versus normal renal cells, normal renal proximal tubule endothelial cells (RPTEC) were treated with ROC-325 for 72 hours under the same conditions that were used for RCC cell lines and quantified its effects on cell viability. In direct contrast to what was observed in RCC cells, treatment of normal renal endothelial cells with ROC-325 resulted in a marginal reduction in cell viability (FIG. 4B). This indicates that ROC-325 may have a favorable therapeutic index. Since the reduction in cell viability observed in RCC cells treated with ROC-325 (FIG. 4A) could have resulted from inhibition of proliferation, cell death, or both, the inventors next quantified the effects of ROC-325 on apoptosis by measuring drug-induced DNA fragmentation and caspase-3 activation. Treatment of RCC cells with ROC-325 for 48 hours led to dose-dependent increases in the percentages of cells with active caspase-3 expression (FIG. 4C) and fragmented DNA (FIG. 4D) in a manner that correlated with the reduction in cell viability. This suggests that the ability of ROC-325 to trigger apoptosis accounts for a significant portion of its anticancer effects.

Oral administration of ROC-325 is well tolerated and antagonizes RCC tumor progression more effectively than HCQ. The in rive anticancer activity of ROC-325 was evaluated by administering vehicle control (water), ROC-325 (25, 40, or 50 mg/kg QD), or HCQ (60 mg/kg QD) to nude mice implanted with 786-0 RCC xenografts. ROC-325 treatment led to significant, dose-dependent inhibition of disease progression in a manner that was superior to HCQ (FIG. 5A). ROC-325 was well tolerated and no notable toxicities were observed other than a very modest, non-significant reduction in mean body weight at the highest dose (FIG. 5B). Immunohistochemical analysis of specimens collected from animals treated with ROC-325 or vehicle control demonstrated significant, dose-dependent increases in the autophagic markers LC3B (FIG. 6A) and p62 (FIG. 6B) and increased apoptosis (cleaved caspase-3, FIG. 6C). The data demonstrate that ROC-325 is orally bioavailable, significantly more efficacious as a monotherapy than HCQ, exhibits favorable tolerability, and inhibits autophagy in vivo. These findings support further investigation of the safety and efficacy of ROC-325 as a novel agent for the treatment of autophagy-driven tumors and other disorders where lysosomal activity contributes to disease pathogenesis.

Discussion

The rational ability of autophagic degradation to help fulfill the fundamental need of tumors to maintain energy metabolism to drive their expansion, metastasis, and sustain their survival under therapy- and microenvironment-induced stress gave rise to a new field focused on determining the contributions of autophagy to malignant pathogenesis. More than a decade later, autophagy has been defined as a mechanism that fuels malignant bioenergetics in a manner that contributes to both disease progression and drug resistance in a diverse range of solid and hematological cancers. Accordingly, a tremendous number of preclinical investigations showed that genetic or pharmacological inhibition of autophagy diminished drug resistance and augmented the efficacy of a plethora of cytotoxic and targeted anticancer agents and radiation therapy. The findings of several of these studies directly established the foundation for multiple early phase clinical trials that investigated the safety and preliminary efficacy of the antimalarial autophagy inhibitor HCQ in combination with several other FDA approved anticancer agents and radiation therapy. The initial series of HCQ combination clinical trials demonstrated that the addition of HCQ to these specific regimens yielded an acceptable safety profile. Preliminary efficacy was observed in a small subset of patients (such as the RCC patient in the HCQ+vorinostat phase I trial) treated in these clinical studies, but the question of whether the MTD of HCQ in these studies resulted in complete autophagic inhibition remained unanswered.

The modest efficacy that was observed in this first series of trials seeking to deliberately inhibit autophagy as a novel therapeutic strategy likely stemmed from two major issues. First, the lack of validated predictive biomarkers that define genetic features of tumors that render them autophagy-dependent prevented the refinement of the eligibility criteria in a way that would facilitate the targeted enrollment of specific patients that may be more likely to benefit from treatment with autophagy inhibitors. It has been reported in preclinical studies that mutations in RAS confer autophagy addiction and that RAS-driven cancers may be hypersensitive to autophagy inhibition. Guo et al., Genes Dev 2011; 25:460-70. However, this has not been clinically proven to date. It is possible that the importance of RAS in this context may be tumor type specific and that other oncogenes with mechanistic links to the control of autophagy may also be involved in determining autophagy dependence. A second major underlying cause of the limited efficacy that the inventors observed is likely due to the pharmacological properties of HCQ itself. HCQ has been used for the treatment of malaria, rheumatoid arthritis and systemic lupus for many years. However, it was not designed to be an autophagy inhibitor. Rather, it has been attempted to be repurposed as such due to the lack of rationally designed autophagy inhibitors available for clinical use and the overwhelming interest to quickly translate the excitement of preclinical findings regarding autophagy inhibition into potential therapeutic benefit for patients with cancer. Thus, the limited clinical efficacy of HCQ in this patient population could be due, in part, to the insufficient inhibition of autophagy at doses of HCQ that yield acceptable safety and tolerability.

The inventors sought to develop new agents that exhibited both superior autophagic inhibition and anticancer activity than HCQ. Since no comprehensive SAR studies determining which chemical motifs are essential to disrupt autophagy at the lysosomal level have been conducted to date, the structure of HCQ and other reported agents that inhibit autophagy was analyzed and a series of new compounds with various modifications to key chemical motifs in HCQ and these other drugs was designed. The initial screening assays identified ROC-325 as a lead compound. Notably, the structure of ROC-325 contains elements of both HCQ and LUC, which the inventors previously discovered to inhibit autophagy, but is chemically distinct from Lys05, another new agent that has been demonstrated to inhibit autophagy. McAfee et al., Proc Natl Acad Sci USA 2012; 109:8253-8.

Comprehensive preclinical studies with ROC-325 demonstrated that it induced all of the hallmark features of genetic and pharmacological autophagy inhibition including the formation of LC3B punctae, accumulation of autophagosomes, stabilization of p62 and disruption of autophagic flux. ROC-325 also triggered the expression of the lysosomal protease CTSD, which the inventors previously showed plays a key role in mediating CQ/HCQ and LUC-induced apoptosis in addition to other genes with established roles in controlling protein degradation and ER stress-induced cell death. Carew et al., J Biol Chem 2011; 286: 6602-13. Although all of these findings are scientifically important and collectively define the mechanism of action of this new drug, the most critical aspect of this study is the evidence demonstrating that ROC-325 is orally bioavailable and inhibits autophagy in vivo while yielding significantly greater single agent efficacy against RCC xenograft tumors than a higher dose of HCQ administered on the same schedule. Collectively, the findings establish ROC-325 as a novel autophagy inhibitor that warrants further investigation to better define its safety and efficacy for the treatment of autophagy-dependent malignancies and other lysosome-centric disorders. IND-enabling studies with ROC-325 are currently underway.

Example II

Synthesis of ROC-325

ROC-325 was prepared according to the reaction scheme shown in FIG. 7. Compound 1 was prepared from 2-bromobenzoic acid and 5-Bromo-2-methylbenzenethiol according to procedures outlined in: Synthesis 2007, No. 22, pp 3519-3527 Regioselective Copper-Catalyzed C—N and C—S Bond Formation Using Amines, Thiols, and Halobenzoic Acids, Shuanglong Liu, John Paul C. Pestano, Christian Wolf.

Compound 2 was prepared from 2,2'-Diamino-N-methyldiethylamine according to procedure outlined in abstract Selective mono-BOC-protection of bispidine, Rawindra Gaware and Ulrich Jordis, 13th electronic conference on synthetic organic chemistry ECSOC-13 Nov. 30, 2009.

Procedure a): A suspension of bromide compound 1 (3.23 g, 10.62 mmoles), amine compound 2 (1.53 g, 7.08 mmoles), Binap (0.88 g, 1.4 mmoles), and $K_3PO_4$ (7.5 g, 35.0 mmoles) in 70 ml of dioxane was purged with $N_2$ for 25 minutes. The reaction was kept under $N_2$ and $Pd(OAc)_2$ (0.159 g, 0.708 mmoles) added. The reaction was heated at 110° C. for 17 hours. The reaction was cooled, dichloromethane (100 ml) added, and the crude mixture filtered and concentrated. Purification by flash silica chromatography eluting with ethyl acetate/hexanes (4:6 to 6:4) provided 1.5 grams of a red solid, compound 3.

$^1$H NMR (400 MHz, CDCl$_3$): δ 10.38 (1H, br s), 8.60 (1H, d), 7.40 (2H, m), 7.36 (1H, m), 7.16 (1H, d), 6.40 (2H, d), 3.30 (2H, m), 3.20 (2H, m), 2.64 (2H, t), 2.58 (2H, t), 2.28 (3H, s), 2.22 (3H, s), 1.4 (9H, s)

Procedure b): To compound 3 (0.53 g) was added 30 ml of 4N HCl. The suspension was stirred at rt for 1.5 hours and the solid collected by filtration, washed with dichloromethane (3×15 ml) and dried at 50° C. to give 150 mg of a red solid, compound 4.

$^1$H NMR (400 MHz, DMSOd6): δ 8.50 (3H, br s), 8.38 (1H, d), 7.70 (1H, d), 7.64 (1H, t), 7.59 (1H, d), 6.81 (1H, d), 3.78 (2H, t), 3.50-3.24 (6H, m), 2.85 (3H, s), 2.24 (3H, s).

Procedure c): Amine 4 (0.250 g, (0.733 mmoles), 4,7-dichloroquinoline (0.329 g, 1.66 mmoles), BINAP (0.091 g, 0.146 mmoles), and K$_3$PO$_4$ (0.778 g, 3.66 mmoles) were suspended in dry dioxane (25 ml). The mixture was purged with N$_2$ for 25 minutes and then kept under N$_2$. Pd(OAc)$_2$ (0.016 g, 0.073 mmoles) was added and the reaction heated for 16 hours at 95° C. The reaction was cooled, and filtered with the aid of dichloromethane (50 ml). The filtrate was concentrated and the crude purified by flash chromatography using ethyl acetate/dichloromethane (1:9) and gave 205 mgs of red foam 6.

Procedure d): The tri-HCl salt of compound 6 was prepared by suspending in 70 ml of methanol, adding 10 ml of 4N HCl in dioxane, and stirring for 15 hours at rt. The precipitate was collected by filtration, washed with methanol, and then ethyl acetate (15/15), and dried at 50° C. under vacuum for 12 hours.

$^1$H NMR (400 MHz, DMSOd6): δ 10.08 (1H, br t), 9.63 (1H, br s), 8.62 (1H, d), 8.48 (1H, d), 8.19 (1H, d), 7.89 (1H, s), 7.64 (2H, m), 7.55 (1H, d), 7.44 (1H, t), 7.25 (1H, d), 6.83 (1H, d), 6.70 (1H, d)), 3.94 (2H, m), 3.76 (2H, m), 3.56 (2H, t), 3.38 (2H, m), 2.96 (3H, s), 2.22 (3H, s)

HRMS: Calcd for C$_{28}$H$_{27}$ClN$_4$OS M+=502.16. Found M+1=503.1682.

Example 3

Alternate Synthesis of ROC-325, and Preparation of Additional Thioxanthenone Compound The reaction scheme for an alternate synthesis of ROC-325 is shown in FIG. 8.

Procedure: A mixture of amine compound 7 (1.397 g, 5.01 mmoles), bromide compound 1 (1.53 g, 5.01 mmoles), K$_3$PO$_4$ (2.12 g, 10.02 mmoles), and BINAP (0.62 g, 1.00 mmoles) in dry dioxane (30 ml) was purged with N$_2$ for 25 minutes at rt and then kept under N$_2$ after the addition of Pd(II)acetate (0.112 g, 0.5 mmoles). The reaction was heated at 90° C. for 15 hours. After cooling to rt, the dioxane was evaporated, and the crude mixture partitioned between dichloromethane (60 ml) and saturated sodium chloride solution (30 ml). The dichloromethane layer was separated, dried over MgSO$_4$, filtered, and concentrated. Flash chromatography using dichloromethane and then dichloromethane/methanol gave 900 mgs of yellow solid, compound 3.

The tri-HCl salt of compound 3 was prepared by suspending in 70 ml of methanol, adding 10 ml of 4N HCl in dioxane, and stirring for 15 hours at rt. The precipitate was collected by filtration, washed with methanol, and then ethyl acetate (15/15), and dried at 50° C. under vacuum for 12 hours.

$^1$H NMR (400 MHz, DMSOd6): δ 10.08 (1H, br t), 9.63 (1H, br s), 8.62 (1H, d), 8.48 (1H, d), 8.19 (1H, d), 7.89 (1H, s), 7.64 (2H, m), 7.55 (1H, d), 7.44 (1H, t), 7.25 (1H, d), 6.83 (1H, d), 6.70 (1H, d)), 3.94 (2H, m), 3.76 (2H, m), 3.56 (2H, t), 3.38 (2H, m), 2.96 (3H, s), 2.22 (3H, s)

HRMS: Calcd for C$_{28}$H$_{27}$ClN$_4$OS M+=502.16. Found M+1=503.1682.

Procedure: A mixture of 4,7-dichloroquinoline (4.22 g, 0.0213 moles), diamine 8 (2.5 g, 0.0213 moles), K$_3$PO$_4$ (8.9 g, 0.042 moles), and BINAP (2.6 g, 4.2 mmoles) in dry dioxane (100 ml) was purged with N$_2$ for 25 minutes at rt and then kept under N$_2$ after the addition of Pd(II)acetate (0.47 g, 2.1 mmoles). The reaction was heated at 90° C. for 17 hours. After cooling to rt, the dioxane was evaporated, and the crude mixture partitioned between dichloromethane (60 ml) and saturated sodium chloride solution (30 ml). The dichloromethane layer was separated, dried over MgSO$_4$, filtered, and concentrated. Flash chromatography (Buchi flash system) using dichloromethane and then dichloromethane:methanol gave 1.39 g of yellow solid, compound 7.

$^1$H NMR (400 MHz, DMSOd6): δ 8.38 (1H, d), 8.34 (1H, d), 7.80 (1H, br s) 7.76 (1H, d), 7.40 (1H, dd), 6.46 (1, d), 3.39 (4H, m), 2.84 (2H, t), 2.62 (2H, t), 2.59 (2H, t), 2.22 (3H, s)

Procedure: A mixture of thiol 9 (3.0 g, 14.78 mmoles), 2-Bromobenzoic acid 10 (2.29 g, 11.4 mmoles), Cu powder (66 mgs), Cu$_2$O (49 mgs), Potassium carbonate (1.57 g, 11.4 mmoles) were heated in 2-ethoxyethanol at 130° C. for 3 hours. The reaction mixture was cooled and 2-ethoxyethanol evaporated. To the crude solid was added ethyl acetate (100 ml). This mixture was filtered to remove insoluble materials and then concentrated. Flash chromatography using ethyl acetate/hexanes gave 1.98 g of white solid 11. This reaction is described in Synthesis 2007, No. 22, pp 3519-3527 Regioselective Copper-Catalyzed C—N and C—S Bond Formation Using Amines. Thiols, and Flalobenzoic Acids, Shuanglong Liu, John Paul C. Pestano, Christian Wolf.

To the acid 11 (1.98 g) was added 10 ml of concentrated H$_2$SO$_4$. This mixture was heated at 100° C. for 1.5 hours, cooled, and added carefully to ice stirring for 1 hour. The solid was collected by filtration, washed with water, dissolved in dichloromethane/methanol 9:1, dried over MgSO$_4$, filtered, and concentrated to give a light yellow solid 1, 1.52 grams.

$^1$H NMR (400 MHz, CDCl$_3$): δ 8.36 (1H, d), 7.46 (2H, min), 7.39 (2H, m), 7.10 (1H, d), 2.38 (3H, s).

Procedure: 2,2'-Diamino N-methyldiethylamine 12 (10.51 g, 89.6 mmoles) was dissolved in methanol (100 ml). The solution was cooled to 0° C. and trifluoroacetic acid (10.21 g) in methanol (30 ml) was added dropwise in 1 hour, 50 ml of water was then added, and the mixture stirred for 1 hour. BOC$_2$O (19.5 g, 89.6 mmoles) and iodine (2.25 g, 8.96 mmoles) in ethanol (75 ml) was added dropwise over 1 hour and then the mixture stirred for 5 hours. The reaction was neutralized with sodium hydroxide solution, concentrated, and the crude partitioned between dichloromethane and water (100 ml/25 ml). The organic layer was separated, the aqueous layer extracted 2× dichloromethane (50 ml), the organic extracts combined, washed with 10% sodium bisulfite solution, and dried over MgSO$_4$. Filtration, and concentration gave crude product which was purified by flash chromatography using dichloromethane/methano/aq NH$_3$ 90:10:2 and gave 8.2 grams of white solid 13.

$^1$H NMR (400 MHz, CDCl$_3$): δ 5.04 (1H, br s), 3.18 (2H, q), 2.70 (2H, t), 2.39 (4H, m), 2.18 (3H, s), 1.77 (2H, br s), 1.40 (9H, s).

Reaction schemes showing the steps involved in the synthesis of additional thioxanthenone autophagy inhibitors are provided by FIG. 9.

Procedure: To solid 3 (0.162 g, 0.379 mmoles) was added 9 ml of 4N HCl in dioxane. After stirring at rt for 2 hours the reaction was concentrated to give an orange solid. To this crude solid was added 12 ml of dichloromethane and then triethylamine (0.115 g, 1.13 mmoles). After 5 minutes, 6-bromo-2-pyridine carboxaldehyde 14 (0.070 g, 0.379 mmoles) was added followed by sodium triacetoxyborohydride (0.104 g, 4.92 mmoles). The reaction mixture was stirred for 12 hours, quenched by addition of saturated sodium bicarbonate solution, and extracted with dichloromethane (2×50 ml). The organic extracts were dried over MgSO$_4$, filtered, and concentrated. Crude product was purified by flash chromatography (Buchi flash, 4 g silica column) using dichloromethane/methanol (95:5). This gave 50 mgs of 15.

$^1$H NMR (400 MHz, CDCl$_3$): δ 10.34 (1H, br s), 8.22 (1H, dd), 7.44 (2H, m), 7.34 (1H, d), 7.26 (1H, m), 7.22 (1H, d) 7.18(1H, d), 7.13(1H, d) 6.46 (1H, d), 3.95(2H, s), 3.28 (2H, q), 2.8(2H, t), 2.74(2H, t), 2.64(2H, t) 2.30(3H, s), 2.28 (3H, s).

$^{13}$C NMR (400 MHz, CDCl$_3$): δ 183.8, 162, 152.4, 141.8, 138.7, 137.9, 136.0, 135.9, 131.8, 130.6, 129.2, 126.0, 125.8, 120.6, 118, 112.7, 107.0, 56.8, 56.2, 54.5, 46.6, 42.1, 40.5, 19.4

Procedure: Amine 4 (0.250 g, 0.733 mmoles), Chloride 16 (0.329 g, 1.099 mmoles), BINAP (0.091 g, 0.146 mmoles), and K$_3$PO$_4$ (0.778 g, 3.66 mmoles) were suspended in dry dioxane (15 ml). The mixture was purged with N$_2$ for 25 minutes and then kept under N$_2$. Pd(OAc)$_2$ (0.016 g, 0.073 mmoles) was added and the reaction heated for 16 hours at 95° C. The reaction was cooled, and filtered with the aid of dichloromethane (50 ml). The filtrate was concentrated and the crude purified by flash chromatography using ethyl acetate/dichloromethane (1:9) and gave 250 mgs of red foam 17.

$^1$H NMR (400 MHz, CDCl$_3$): δ 8.16 (2H, d), 7.70 (1H, d), 7.48 (2H, m), 7.20 (3H, m), 6.84 (1H, t) 6.68(2H, br s) 6.46 (1H, d), 3.45 (2H, q), 3.38(2H, q), 2.84(4H, m), 2.40(3H, s), 2.30(3H, s)

Procedure: Amine 4 (0.143 g, 0.93 mmoles), Chloride 18 (0.143 g), BINAP (0.115 g, 0.186 mmoles), and K$_3$PO$_4$ (0.395 g, 1.86 mmoles) were suspended in dry dioxane (15 ml). The mixture was purged with N$_2$ for 25 minutes and then kept under N$_2$. Pd(OAc)$_2$ (0.021 g, 0.093 mmoles) was added and the reaction heated for 18 hours at 90° C. The reaction was cooled, and filtered with the aid of dichloromethane (50 ml). The filtrate was concentrated and the crude purified by tlc chromatography using dichloromethane/methanol (9:1) and gave 40 mgs of red foam 19.

$^1$H NMR (400 MHz, CDCl$_3$): δ 8.46 (1H, d), 8.42 (1H, s), 7.60 (2H, m), 7.44 (1H, m), 7.26 (1H, d), 6.64(1H, m), 6.54 (1H, d) 6.40(2H, br s), 3.79 (2H, q), 3.36(2H, q), 2.80(4H, m), 2.37(3H, s), 2.29(3H, s)

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A compound of formula I

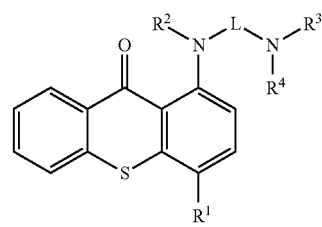

wherein R$^1$ is a group selected from lower alkyl, lower alkyl amide, lower alkyl ester, lower alkyl ketone, and lower alkyl ether; R$^2$ and R$^3$ are H or a group selected from cycloalkyl, lower alkyl, lower alkyl amide, lower alkyl ester, lower alkyl ketone, and lower alkyl ether; R$^4$ is a heteroaryl group; and L is —CH$_2$—CH$_2$—N(CH$_3$)—CH$_2$—CH$_2$, or a pharmaceutically acceptable salt thereof.

2. The compound of claim 1, wherein the heteroaryl group is a quinolinyl, pyridyl, or substituted anthracenyl compound.

3. The compound of claim 2, wherein the anthracenyl compound is an anthracenyl dione or thioxantheninyl compound.

4. The compound of claim 1, wherein the heteroaryl group is selected from the group consisting of:

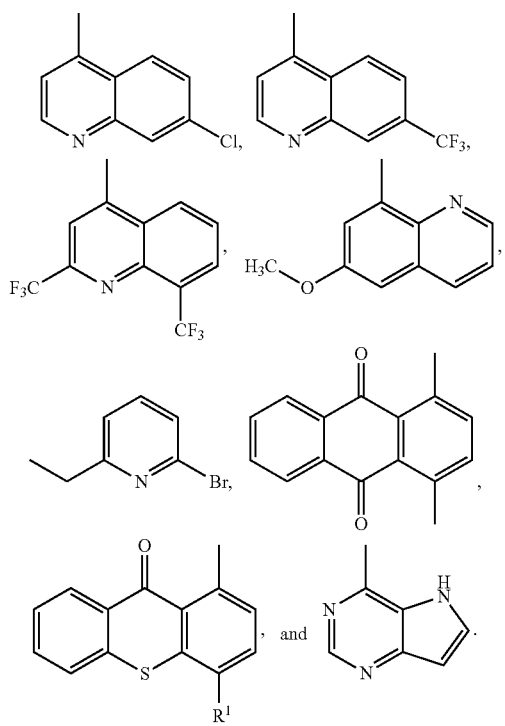

5. The compound of claim 1, wherein R$^1$ is lower alkyl.

6. The compound of claim 1, wherein the compound has the structure:

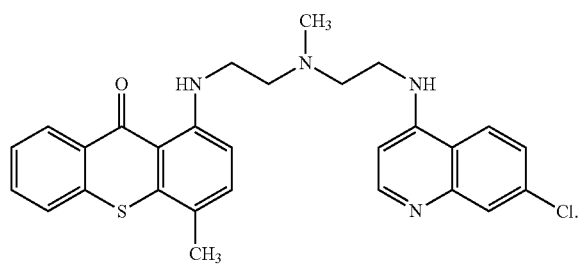 [SMILES: Cc1ccc(NCCN(C)CCNc2ccnc3cc(Cl)ccc23)c2c(=O)c3ccccc3sc12]

7. A method of treating a disease or condition that responds favorably to autophagy inhibition in a subject in need thereof by administering a therapeutically effective amount of a compound of Formula I:

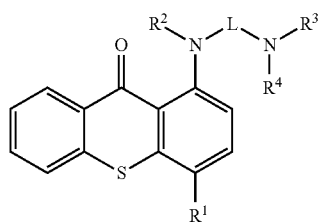

wherein $R^1$ is a group selected from lower alkyl, lower alkyl amide, lower alkyl ester, lower alkyl ketone, and lower alkyl ether; $R^2$ and $R^3$ are H or a group selected from cycloalkyl, lower alkyl, lower alkyl amide, lower alkyl ester, lower alkyl ketone, and lower alkyl ether; $R^4$ is a heteroaryl group; and L is a —$(CH_2)_n$—X—$(CH_2)_n$— group, wherein n is 1, 2, 3, or 4, X is absent, O, S, or N—$R^5$, wherein $R^5$ is H or a lower alkyl group, or a pharmaceutically acceptable salt thereof wherein the disease or condition is selected from the group consisting of cancer, rheumatoid arthritis, diabetes, malaria, schistosomiasis, antiphospolipid antibody syndrome, lupus, chronic urticaria, Sjogren's disease, reperfusion injury, Huntington's disease, Alzheimer's disease, Parkinson's disease, and amyotrophic lateral sclerosis.

8. The method of claim 7, wherein the disease or condition is cancer.

9. The method of claim 8, wherein the cancer is leukemia.

10. The method of claim 8, wherein the method further comprises administration of an additional anticancer agent.

11. The method of claim 7, wherein the heteroaryl group is a quinolinyl, pyridyl, or substituted anthracenyl compound.

12. The method of claim 11, wherein the substituted anthracenyl compound is an anthracenyl dione or thioxantheninyl compound.

13. The method of claim 7, wherein the heteroaryl group is selected from the group consisting of:

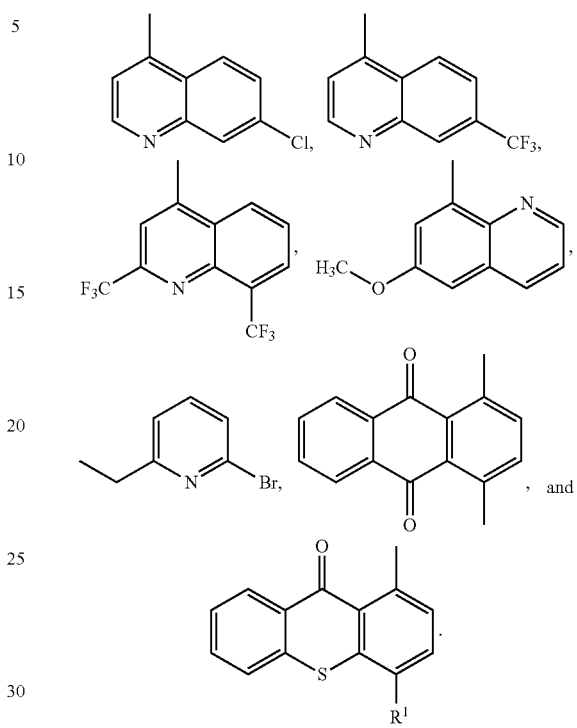

14. The method of claim 7, wherein $R^1$ is lower alkyl.

15. The method of claim 7, wherein L is —$CH_2$—$CH_2$—$N(CH_3)$—$CH_2$—$CH_2$—.

16. The method of claim 7, wherein the compound has the structure:

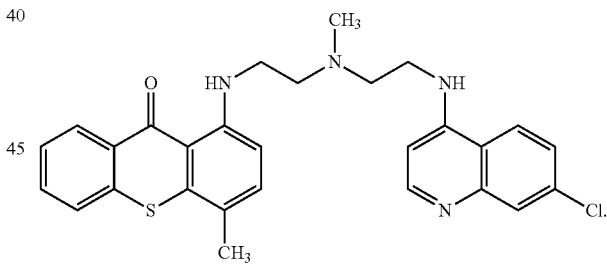

17. The method of claim 7, wherein the compound is administered in a pharmaceutically acceptable carrier.

* * * * *